US009034014B2

(12) United States Patent
Catania et al.

(10) Patent No.: US 9,034,014 B2
(45) Date of Patent: May 19, 2015

(54) FREE FLOATING WEDGE SUTURE ANCHOR FOR SOFT TISSUE REPAIR

(75) Inventors: Pablo Catania, Costa Mesa, CA (US); Steven Wolf, Mission Viejo, CA (US); Emil Karapetian, Huntington Beach, CA (US); George W. White, Corona, CA (US); David Gregoire, Mission Viejo, CA (US); Seth A. Foerster, San Clemente, CA (US); Christopher Rodriguez, Costa Mesa, CA (US)

(73) Assignee: ArthroCare Corporation, Austin, TX (US)

( * ) Notice: Subject to any disclaimer, the term of this patent is extended or adjusted under 35 U.S.C. 154(b) by 604 days.

(21) Appl. No.: 13/359,642

(22) Filed: Jan. 27, 2012

(65) Prior Publication Data
US 2013/0197576 A1 Aug. 1, 2013

(51) Int. Cl.
A61B 17/04 (2006.01)

(52) U.S. Cl.
CPC ..... *A61B 17/0401* (2013.01); *A61B 2017/0409* (2013.01); *A61B 2017/0412* (2013.01); *A61B 2017/0422* (2013.01); *A61B 2017/0451* (2013.01); *A61B 2017/0496* (2013.01)

(58) Field of Classification Search
CPC .......... A61B 17/0401; A61B 2017/0414; A61B 2017/0451; A61B 2017/0456; A61B 2017/0446; A61B 2017/0448
USPC .......... 606/232
See application file for complete search history.

(56) References Cited

U.S. PATENT DOCUMENTS

| 918,570 | A | 4/1909 | Mather | 292/318 |
|---|---|---|---|---|
| 1,153,053 | A | 9/1915 | Forster | 43/44.85 |
| 1,565,041 | A | 12/1925 | Arneu | 24/129 R |
| 2,269,963 | A | 1/1942 | Wrapler | 604/604 |
| 2,485,531 | A | 10/1949 | Dzus et al. | 128/92 |
| 2,600,395 | A | 6/1952 | Domoj et al. | 87/13 |
| 3,143,916 | A | 8/1964 | Rice | 85/71 |
| 3,942,407 | A | 3/1976 | Mortensen | 85/71 |
| 3,946,740 | A | 3/1976 | Bassett | 128/334 |
| 3,994,521 | A | 11/1976 | Van Gompel | 292/319 |
| 4,109,658 | A | 8/1978 | Hughes | 128/340 |
| 4,210,148 | A | 7/1980 | Stivala | 606/232 |
| 4,274,324 | A | 6/1981 | Giannuzzi | 411/38 |

(Continued)

FOREIGN PATENT DOCUMENTS

| DE | 3509417 | 9/1986 | ............ A61B 17/58 |
|---|---|---|---|
| EP | 0 535 906 A2 | 4/1993 | ............ A61B 17/04 |

(Continued)

OTHER PUBLICATIONS

PCT Search Report and Written Opinion for PCT/US06/20657 7pgs Mailed Oct. 2, 2007.

(Continued)

*Primary Examiner* — Kathleen Holwerda
(74) *Attorney, Agent, or Firm* — Norman F. Hainer, Jr.

(57) ABSTRACT

A suture anchor device and method for attaching soft tissue to bone includes an anchor body and a suture locking wedge movably disposed within the anchor body. The suture locking wedge includes lateral portions which engage slots or windows in the anchor body. Tension applied to one limb of a suture causes the suture locking wedge to translate and rotate to a position which compresses the suture, thereby locking the suture in the anchor.

31 Claims, 14 Drawing Sheets

(56) References Cited

U.S. PATENT DOCUMENTS

| | | | | |
|---|---|---|---|---|
| 4,301,551 A | 11/1981 | Dore et al. | | 623/13.3 |
| 4,319,428 A | 3/1982 | Fox | | 47/42 |
| 4,345,601 A | 8/1982 | Fukuda | | 128/339 |
| 4,373,530 A | 2/1983 | Kilejian | | 128/334 R |
| 4,384,389 A | 5/1983 | Sato | | 24/136 K |
| 4,409,974 A | 10/1983 | Freedland | | 128/92 |
| 4,456,270 A | 6/1984 | Zettl, et al. | | 279/62 |
| 4,467,478 A | 8/1984 | Jurgutis | | 606/75 |
| 4,483,023 A | 11/1984 | Hoffman, Jr. et al. | | 623/13.15 |
| 4,493,323 A | 1/1985 | Albright et al. | | 128/340 |
| 4,580,936 A | 4/1986 | Francis et al. | | 411/38 |
| 4,590,928 A | 5/1986 | Hunt et al. | | 606/72 |
| 4,597,776 A | 7/1986 | Ullman et al. | | 48/197 R |
| 4,605,414 A | 8/1986 | Czajka | | 623/13.11 |
| 4,621,640 A | 11/1986 | Mulhollan et al. | | 128/340 |
| 4,635,637 A | 1/1987 | Schreiber | | 128/337 |
| 4,657,461 A | 4/1987 | Smith | | 411/340 |
| 4,672,957 A | 6/1987 | Hourahane | | 606/80 |
| 4,680,835 A | 7/1987 | Horng | | 24/712.5 |
| 4,712,542 A | 12/1987 | Daniel et al. | | 606/96 |
| 4,721,103 A | 1/1988 | Freedland | | 128/92 |
| 4,731,084 A | 3/1988 | Dunn et al. | | 623/13.19 |
| 4,738,255 A | 4/1988 | Goble et al. | | 128/92 YF |
| 4,741,330 A | 5/1988 | Hayhurst | | 123/43 R |
| 4,750,492 A | 6/1988 | Jacobs | | 606/230 |
| 4,772,286 A | 9/1988 | Goble et al. | | 623/13.14 |
| 4,779,616 A | 10/1988 | Johnson et al. | | 606/148 |
| 4,809,408 A | 3/1989 | Abrahamson | | 24/136 K |
| 4,823,780 A | 4/1989 | Odensten et al. | | 606/96 |
| 4,828,439 A | 5/1989 | Giannuzzi | | 411/37 |
| 4,851,005 A | 7/1989 | Hunt et al. | | 623/18 |
| 4,870,957 A | 10/1989 | Goble et al. | | 606/73 |
| 4,917,700 A | 4/1990 | Aikins | | 623/13.19 |
| 4,926,860 A | 5/1990 | Stice et al. | | 606/144 |
| 4,935,027 A | 6/1990 | Yoon | | 606/146 |
| 4,946,467 A | 8/1990 | Ohi et al. | | 606/228 |
| 4,946,468 A | 8/1990 | Li | | 606/232 |
| 4,957,498 A | 9/1990 | Caspari et al. | | 606/146 |
| 4,968,315 A | 11/1990 | Gatturna | | 606/72 |
| 4,981,149 A | 1/1991 | Yoon et al. | | 128/898 |
| 4,987,665 A | 1/1991 | Dumican et al. | | 28/218 |
| 5,002,550 A | 3/1991 | Li | | 606/139 |
| 5,019,093 A | 5/1991 | Kaplan et al. | | 606/228 |
| 5,037,422 A | 8/1991 | Hayhurst | | 606/72 |
| 5,046,513 A | 9/1991 | Gatturna | | 128/898 |
| 5,059,201 A | 10/1991 | Asnis | | 606/144 |
| 5,062,344 A | 11/1991 | Gerker | | 87/8 |
| 5,085,661 A | 2/1992 | Moss | | 606/139 |
| 5,147,166 A | 9/1992 | Harker | | 411/29 |
| 5,195,542 A | 3/1993 | Gazielly et al. | | 60/244 |
| 5,203,787 A | 4/1993 | Noblitt et al. | | 606/232 |
| RE34,293 E | 6/1993 | Goble et al. | | |
| 5,217,495 A | 6/1993 | Kaplan et al. | | 623/13.18 |
| 5,219,359 A | 6/1993 | McQuilkin et al. | | 606/232 |
| 5,224,946 A | 7/1993 | Hayhurst et al. | | 606/72 |
| 5,258,016 A | 11/1993 | DiPoto et al. | | 606/232 |
| 5,263,984 A | 11/1993 | Li | | 623/13.18 |
| 5,275,176 A | 1/1994 | Chandler | | 606/242 |
| 5,304,184 A | 4/1994 | Hathaway et al. | | 606/144 |
| 5,306,290 A | 4/1994 | Martins et al. | | 606/232 |
| 5,324,308 A | 6/1994 | Pierce | | 606/232 |
| 5,326,205 A | 7/1994 | Anspach, III et al. | | 411/43 |
| 5,330,442 A | 7/1994 | Green | | 606/232 |
| 5,330,468 A | 7/1994 | Burkhart | | 606/96 |
| 5,330,488 A | 7/1994 | Goldrath | | 606/148 |
| 5,336,240 A | 8/1994 | Metzler et al. | | 606/232 |
| 5,354,298 A | 10/1994 | Lee et al. | | 606/72 |
| 5,364,407 A | 11/1994 | Poll | | 606/139 |
| 5,376,118 A | 12/1994 | Kaplan et al. | | 623/23.72 |
| 5,383,905 A | 1/1995 | Gold et al. | | 606/232 |
| 5,405,352 A | 4/1995 | Weston | | 606/148 |
| 5,405,359 A | 4/1995 | Pierce | | 606/232 |
| 5,411,523 A | 5/1995 | Goble | | 606/232 |
| 5,413,579 A | 5/1995 | Tom Du | | 606/87 |
| 5,417,691 A | 5/1995 | Hayhurst | | 606/72 |
| 5,417,699 A | 5/1995 | Klein et al. | | 606/139 |
| 5,417,712 A | 5/1995 | Whittaker et al. | | 606/232 |
| 5,431,666 A | 7/1995 | Sauer et al. | | 606/139 |
| 5,441,508 A | 8/1995 | Gazielly et al. | | 606/151 |
| 5,445,167 A | 8/1995 | Yoon et al. | | 128/898 |
| 5,450,860 A | 9/1995 | O'Connor | | 606/224 |
| 5,454,823 A | 10/1995 | Richardson et al. | | 606/148 |
| 5,464,427 A | 11/1995 | Curtis et al. | | 606/232 |
| 5,470,335 A | 11/1995 | DuToit | | 606/73 |
| 5,472,452 A | 12/1995 | Trott | | 606/232 |
| 5,480,403 A | 1/1996 | Lee et al. | | 606/72 |
| 5,486,197 A | 1/1996 | Le et al. | | 606/232 |
| 5,499,991 A | 3/1996 | Garman et al. | | 606/148 |
| 5,501,683 A | 3/1996 | Trott | | 606/72 |
| 5,501,695 A | 3/1996 | Anspach, Jr. et al. | | 606/72 |
| 5,505,735 A | 4/1996 | Li | | 606/72 |
| 5,514,159 A | 5/1996 | Matula et al. | | 606/232 |
| 5,520,700 A | 5/1996 | Beyar et al. | | 606/139 |
| 5,522,820 A | 6/1996 | Caspari et al. | | 606/148 |
| 5,527,322 A | 6/1996 | Klein et al. | | 606/144 |
| 5,527,343 A | 6/1996 | Bonutti | | 606/232 |
| 5,531,763 A | 7/1996 | Mastri et al. | | 606/148 |
| 5,531,792 A | 7/1996 | Huene | | 623/16 |
| 5,534,012 A | 7/1996 | Bonutti | | 606/232 |
| 5,540,703 A | 7/1996 | Barker, Jr. et al. | | 606/139 |
| 5,545,180 A | 8/1996 | Le et al. | | 606/232 |
| 5,549,617 A | 8/1996 | Green et al. | | 606/144 |
| 5,549,630 A | 8/1996 | Bonutti | | 606/232 |
| 5,553,360 A | 9/1996 | Lucas et al. | | 24/136 K |
| 5,562,689 A * | 10/1996 | Green et al. | | 606/151 |
| 5,569,305 A | 10/1996 | Bonutti | | 606/232 |
| 5,569,306 A | 10/1996 | Thal | | 606/232 |
| 5,571,104 A | 11/1996 | Li | | 606/72 |
| 5,571,120 A | 11/1996 | Yoon | | 606/148 |
| 5,573,540 A | 11/1996 | Yoon | | 606/139 |
| 5,573,542 A | 11/1996 | Stevens | | 606/144 |
| 5,573,548 A | 11/1996 | Nazre et al. | | 606/232 |
| 5,575,801 A | 11/1996 | Habermeyer et al. | | 606/148 |
| 5,584,835 A | 12/1996 | Greenfield | | 606/73 |
| 5,584,839 A | 12/1996 | Gieringer | | 606/96 |
| 5,584,860 A | 12/1996 | Goble et al. | | 606/232 |
| 5,584,862 A | 12/1996 | Bonutti | | 606/232 |
| 5,591,207 A | 1/1997 | Coleman | | 606/232 |
| 5,593,189 A | 1/1997 | Little | | 289/17 |
| 5,601,558 A | 2/1997 | Torrie et al. | | 606/72 |
| 5,609,597 A | 3/1997 | Lehrer | | 606/139 |
| 5,611,801 A | 3/1997 | Songer | | 606/73 |
| 5,613,974 A | 3/1997 | Andreas et al. | | 606/144 |
| 5,618,290 A | 4/1997 | Toy et al. | | 606/139 |
| 5,618,314 A | 4/1997 | Harwin et al. | | 606/232 |
| 5,626,614 A | 5/1997 | Hart | | 606/232 |
| 5,630,824 A | 5/1997 | Hart | | 606/139 |
| 5,632,748 A | 5/1997 | Beck, Jr. et al. | | 606/72 |
| 5,645,589 A | 7/1997 | Li | | 623/16 |
| 5,647,874 A | 7/1997 | Hayhurst | | 606/72 |
| 5,649,940 A | 7/1997 | Hart et al. | | 606/148 |
| 5,649,963 A | 7/1997 | McDevitt | | 606/232 |
| 5,658,313 A | 8/1997 | Thal | | 606/232 |
| 5,665,110 A | 9/1997 | Chervitz et al. | | 606/232 |
| 5,665,112 A | 9/1997 | Thal | | 606/232 |
| 5,667,528 A | 9/1997 | Colligan | | 606/224 |
| D385,352 S | 10/1997 | Bales et al. | | D24/145 |
| 5,681,333 A | 10/1997 | Burkhart et al. | | 606/148 |
| 5,681,351 A | 10/1997 | Jamiolkowski et al. | | 606/232 |
| 5,683,418 A | 11/1997 | Luscombe et al. | | 606/232 |
| 5,683,419 A | 11/1997 | Thal | | 606/232 |
| 5,690,649 A | 11/1997 | Li | | 606/139 |
| 5,693,060 A | 12/1997 | Martin | | 606/148 |
| 5,697,950 A | 12/1997 | Fucci et al. | | 606/232 |
| 5,702,397 A * | 12/1997 | Goble et al. | | 606/232 |
| 5,702,398 A | 12/1997 | Tarabishy | | |
| 5,707,362 A | 1/1998 | Yoon | | 604/164 |
| 5,707,394 A | 1/1998 | Miller et al. | | 606/232 |
| 5,709,708 A | 1/1998 | Thal | | 606/232 |
| 5,720,765 A | 2/1998 | Thal | | 606/232 |
| 5,725,529 A | 3/1998 | Nicholson et al. | | 606/72 |
| 5,725,541 A | 3/1998 | Anspach, III et al. | | 606/151 |
| 5,728,136 A | 3/1998 | Thal | | 606/232 |
| 5,733,307 A | 3/1998 | Dinsdale | | 606/232 |

(56) References Cited

U.S. PATENT DOCUMENTS

| | | | |
|---|---|---|---|
| 5,741,281 A | 4/1998 | Martin | 606/148 |
| 5,741,282 A | 4/1998 | Anspach, III et al. | 606/151 |
| 5,766,250 A | 6/1998 | Chervitz et al. | 623/13 |
| 5,782,863 A | 7/1998 | Bartlett | 606/232 |
| 5,782,864 A | 7/1998 | Lizardi | 606/232 |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |
| 5,797,927 A | 8/1998 | Yoon | 606/144 |
| 5,797,963 A | 8/1998 | McDevitt | 606/232 |
| 5,810,848 A | 9/1998 | Hayhurst | 606/144 |
| 5,810,854 A | 9/1998 | Beach | 606/232 |
| 5,814,052 A | 9/1998 | Nakao et al. | 606/148 |
| 5,814,071 A | 9/1998 | McDevitt et al. | 606/232 |
| 5,814,072 A | 9/1998 | Bonutti | 606/232 |
| 5,843,111 A | 12/1998 | Vijfvinkel | 606/171 |
| 5,849,004 A | 12/1998 | Bramlet | 606/232 |
| 5,860,978 A | 1/1999 | McDevitt | 606/72 |
| 5,860,991 A | 1/1999 | Klein et al. | 606/144 |
| 5,860,992 A | 1/1999 | Daniel et al. | 606/145 |
| 5,868,789 A | 2/1999 | Huebner | 606/232 |
| 5,879,372 A | 3/1999 | Bartlett | 606/232 |
| 5,882,340 A | 3/1999 | Yoon | 604/164 |
| 5,885,294 A | 3/1999 | Pedlick et al. | 606/80 |
| 5,891,168 A | 4/1999 | Thal | 606/232 |
| 5,893,850 A | 4/1999 | Cachia | 606/72 |
| 5,902,311 A | 5/1999 | Andreas et al. | 606/144 |
| 5,904,692 A | 5/1999 | Steckel et al. | 606/139 |
| 5,911,721 A | 6/1999 | Nicholson et al. | 606/72 |
| 5,921,994 A | 7/1999 | Andreas et al. | 606/144 |
| 5,935,107 A | 8/1999 | Taylor et al. | 604/164 |
| 5,935,129 A | 8/1999 | McDevitt | 606/72 |
| 5,941,900 A | 8/1999 | Bonutti | 606/232 |
| 5,941,901 A | 8/1999 | Egan | 606/232 |
| 5,944,724 A | 8/1999 | Lizardi | 606/104 |
| 5,944,739 A | 8/1999 | Zlock et al. | 606/232 |
| 5,947,982 A | 9/1999 | Duran | 606/139 |
| 5,948,000 A | 9/1999 | Larsen et al. | 606/232 |
| 5,948,001 A | 9/1999 | Larsen | 606/232 |
| 5,948,002 A | 9/1999 | Bonutti | 606/232 |
| 5,957,953 A | 9/1999 | DiPoto et al. | 606/232 |
| 5,957,968 A | 9/1999 | Belden et al. | 607/126 |
| 5,961,530 A | 10/1999 | Moore et al. | 606/148 |
| 5,961,538 A | 10/1999 | Pedlick et al. | 606/232 |
| 5,968,044 A | 10/1999 | Nicholson et al. | 606/72 |
| 5,980,558 A | 11/1999 | Wiley | 606/232 |
| 5,980,559 A | 11/1999 | Bonutti | 606/232 |
| 5,984,933 A | 11/1999 | Yoon | 606/148 |
| 5,993,459 A | 11/1999 | Larsen | 606/104 |
| 6,001,104 A | 12/1999 | Benderev et al. | 606/80 |
| 6,001,109 A | 12/1999 | Kontos | 606/148 |
| 6,007,566 A | 12/1999 | Wenstrom | 606/232 |
| 6,007,567 A | 12/1999 | Bonutti | 606/232 |
| 6,010,525 A | 1/2000 | Bonutti et al. | 606/232 |
| 6,013,083 A | 1/2000 | Bennett | 606/104 |
| 6,017,346 A | 1/2000 | Grotz | 606/72 |
| 6,022,360 A | 2/2000 | Reimels et al. | 606/144 |
| 6,022,373 A | 2/2000 | Li | 606/232 |
| 6,024,758 A | 2/2000 | Thal | 606/232 |
| 6,033,430 A | 3/2000 | Bonutti | 606/232 |
| 6,036,699 A | 3/2000 | Andreas et al. | 606/139 |
| 6,045,571 A | 4/2000 | Hill et al. | 606/228 |
| 6,045,572 A | 4/2000 | Johnson et al. | 606/232 |
| 6,045,573 A | 4/2000 | Wenstrom et al. | 606/232 |
| 6,045,574 A | 4/2000 | Thal | 606/232 |
| 6,048,351 A | 4/2000 | Gordon et al. | 606/144 |
| 6,051,006 A | 4/2000 | Shluzas et al. | 606/148 |
| 6,053,935 A | 4/2000 | Brenneman et al. | 606/232 |
| 6,056,773 A | 5/2000 | Bonutti | 606/232 |
| 6,066,146 A | 5/2000 | Carroll et al. | 606/148 |
| 6,066,160 A * | 5/2000 | Colvin et al. | 606/232 |
| 6,068,648 A | 5/2000 | Cole et al. | 606/232 |
| 6,086,608 A | 7/2000 | Elk et al. | 606/232 |
| 6,096,051 A | 8/2000 | Kortenbach et al. | 606/144 |
| 6,102,934 A | 8/2000 | Li | 606/232 |
| 6,117,160 A | 9/2000 | Bonutti | 606/215 |
| 6,117,161 A | 9/2000 | Li | 606/232 |
| 6,143,004 A | 11/2000 | Davis et al. | 606/144 |
| 6,146,386 A | 11/2000 | Blackman | 606/103 |
| 6,146,406 A | 11/2000 | Shluzas et al. | 606/232 |
| 6,149,669 A | 11/2000 | Li | 606/232 |
| 6,156,039 A | 12/2000 | Thal | 606/72 |
| 6,156,056 A | 12/2000 | Kearns et al. | 606/232 |
| 6,159,235 A | 12/2000 | Kim | 606/232 |
| 6,162,537 A | 12/2000 | Martin et al. | 428/373 |
| 6,171,317 B1 | 1/2001 | Jackson et al. | 606/148 |
| 6,200,329 B1 | 3/2001 | Fung et al. | 606/232 |
| 6,200,893 B1 | 3/2001 | Sneh | 438/685 |
| 6,206,895 B1 | 3/2001 | Levinson | 606/144 |
| 6,217,592 B1 | 4/2001 | Freda et al. | 606/145 |
| 6,221,107 B1 | 4/2001 | Steiner et al. | 623/13.14 |
| 6,228,096 B1 | 5/2001 | Marchand | 606/139 |
| 6,241,736 B1 | 6/2001 | Sater | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz | 606/232 |
| 6,295,700 B1 | 10/2001 | Plzak | 24/134 R |
| 6,315,781 B1 | 11/2001 | Reinhardt | 606/108 |
| 6,319,252 B1 | 11/2001 | McDevitt et al. | 606/60 |
| 6,319,269 B1 | 11/2001 | Li | 606/232 |
| 6,319,271 B1 | 11/2001 | Schwartz | 606/232 |
| 6,328,758 B1 | 12/2001 | Tornier et al. | 606/232 |
| 6,355,053 B1 | 3/2002 | Li | 606/232 |
| 6,409,743 B1 | 6/2002 | Fenton | 606/232 |
| 6,432,123 B2 | 8/2002 | Schwartz et al. | 606/232 |
| 6,436,109 B1 | 8/2002 | Kontes | 606/148 |
| 6,451,030 B2 | 9/2002 | Li et al. | 606/139 |
| 6,464,713 B2 | 10/2002 | Bonutti | 606/232 |
| 6,468,293 B2 | 10/2002 | Bonutti et al. | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,517,542 B1 | 2/2003 | Papay et al. | 606/73 |
| 6,520,980 B1 | 2/2003 | Foerster | 606/232 |
| 6,524,317 B1 | 2/2003 | Ritchart et al. | 606/72 |
| 6,527,794 B1 | 3/2003 | McDevitt et al. | 606/232 |
| 6,540,770 B1 | 4/2003 | Tornier et al. | 606/232 |
| 6,569,187 B1 | 5/2003 | Bonutti et al. | 606/232 |
| 6,575,987 B2 | 6/2003 | Gellman et al. | 606/151 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson, III | 606/232 |
| 6,652,561 B1 | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | 606/232 |
| 6,673,094 B1 | 1/2004 | McDevitt et al. | 606/232 |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,887,259 B2 | 5/2005 | Lizardi | 606/232 |
| 6,939,379 B2 | 9/2005 | Sklar | 623/13.14 |
| 6,972,027 B2 | 12/2005 | Fallin et al. | 606/232 |
| 7,083,638 B2 | 8/2006 | Foerster | 606/232 |
| 7,087,064 B1 | 8/2006 | Hyde | 606/142 |
| 7,090,690 B2 | 8/2006 | Foerster et al. | 606/232 |
| 7,104,999 B2 | 9/2006 | Overaker | 606/142 |
| 7,144,415 B2 | 12/2006 | Del Rio et al. | 606/232 |
| 7,150,750 B2 | 12/2006 | Damarati | 623/17.11 |
| 7,150,757 B2 | 12/2006 | Fallin et al. | 606/232 |
| 7,247,164 B1 | 7/2007 | Ritchart et al. | 606/232 |
| 7,320,701 B2 | 1/2008 | Haut et al. | 606/232 |
| 7,329,272 B2 | 2/2008 | Burkhart et al. | 606/232 |
| 7,381,213 B2 | 6/2008 | Lizardi | 606/232 |
| 7,410,489 B2 | 8/2008 | Dakin et al. | 606/103 |

(56) References Cited

U.S. PATENT DOCUMENTS

| | | | |
|---|---|---|---|
| 7,556,640 B2 | 7/2009 | Foerster | 606/232 |
| 7,588,587 B2 | 9/2009 | Barbieri et al. | 606/232 |
| 7,615,061 B2 | 11/2009 | White et al. | 606/148 |
| 7,637,926 B2 | 12/2009 | Foerster et al. | 606/232 |
| 7,674,274 B2 | 3/2010 | Foerster et al. | 606/232 |
| 7,682,374 B2 | 3/2010 | Foerster | 606/72 |
| 7,695,494 B2 | 4/2010 | Foerster | 606/232 |
| 7,837,710 B2 | 11/2010 | Lombardo et al. | 606/232 |
| 7,867,251 B2 | 1/2011 | Colleran et al. | 606/232 |
| 7,938,847 B2 * | 5/2011 | Fanton et al. | 606/232 |
| 7,963,972 B2 | 6/2011 | Foerster et al. | 606/139 |
| 7,981,140 B2 | 7/2011 | Burkhart | 606/232 |
| 8,109,966 B2 | 2/2012 | Ritchart et al. | 606/232 |
| 8,133,258 B2 | 3/2012 | Foerster et al. | 606/232 |
| 8,137,381 B2 | 3/2012 | Foerster et al. | 606/232 |
| 8,317,829 B2 | 11/2012 | Foerster et al. | 606/232 |
| 8,425,536 B2 | 4/2013 | Foerster et al. | 606/232 |
| 8,444,672 B2 | 5/2013 | Foerster | 606/232 |
| 8,657,854 B2 | 2/2014 | Foerster et al. | 606/232 |
| 8,685,060 B2 | 4/2014 | Foerster | 606/232 |
| 2003/0105489 A1 | 6/2003 | Eichhorn et al. | 606/232 |
| 2003/0167062 A1 | 9/2003 | Gambale | 606/232 |
| 2003/0195563 A1 | 10/2003 | Foerster | 606/232 |
| 2003/0195564 A1 | 10/2003 | Tran et al. | 606/232 |
| 2004/0133239 A1 | 7/2004 | Singhatat | 606/232 |
| 2004/0138683 A1 | 7/2004 | Shelton et al. | 606/151 |
| 2004/0138706 A1 | 7/2004 | Abrams et al. | 606/232 |
| 2004/0153074 A1 | 8/2004 | Bojarski et al. | 606/232 |
| 2004/0236336 A1 | 11/2004 | Foerster et al. | 606/72 |
| 2005/0033364 A1 | 2/2005 | Gregoire et al. | 606/232 |
| 2005/0080455 A1 | 4/2005 | Schmieding et al. | 606/232 |
| 2005/0090827 A1 | 4/2005 | Gedebou | 606/72 |
| 2005/0273101 A1 | 12/2005 | Schumacher | 606/61 |
| 2005/0277986 A1 | 12/2005 | Foerster | 606/232 |
| 2006/0004364 A1 | 1/2006 | Green et al. | 606/72 |
| 2006/0074422 A1 | 4/2006 | Story et al. | 606/142 |
| 2006/0079904 A1 | 4/2006 | Thal | 606/72 |
| 2006/0106423 A1 | 5/2006 | Weisel et al. | 606/232 |
| 2006/0161159 A1 | 7/2006 | Dreyfuss et al. | 606/72 |
| 2006/0271060 A1 | 11/2006 | Gordon | 606/232 |
| 2006/0271105 A1 | 11/2006 | Foerster et al. | 606/232 |
| 2006/0282081 A1 | 12/2006 | Fanton et al. | 606/232 |
| 2007/0055379 A1 | 3/2007 | Stone et al. | 606/75 |
| 2007/0142838 A1 | 6/2007 | Jordan | 606/75 |
| 2007/0156148 A1 | 7/2007 | Fanton et al. | 606/72 |
| 2008/0051836 A1 | 2/2008 | Foerster et al. | 606/232 |
| 2008/0119849 A1 | 5/2008 | Beardsley et al. | 606/61 |
| 2008/0319478 A1 | 12/2008 | Foerster et al. | 606/148 |
| 2009/0069823 A1 | 3/2009 | Foerster et al. | 606/103 |
| 2009/0222040 A1 | 9/2009 | Foerster et al. | 606/232 |
| 2009/0222041 A1 | 9/2009 | Foerster et al. | 606/232 |
| 2009/0248068 A1 | 10/2009 | Lombardo et al. | 606/232 |
| 2010/0191283 A1 | 7/2010 | Foerster et al. | 606/232 |
| 2013/0060280 A1 | 3/2013 | Wolf et al. | 606/232 |
| 2013/0197575 A1 | 8/2013 | Karapetian et al. | 606/232 |
| 2013/0197577 A1 | 8/2013 | Wolf et al. | 606/232 |
| 2013/0197578 A1 | 8/2013 | Gregoire et al. | 606/232 |
| 2013/0197579 A1 | 8/2013 | Foerster et al. | 606/232 |
| 2013/0267998 A1 | 10/2013 | Vijay et al. | 606/232 |
| 2014/0207189 A1 | 7/2014 | Foerster et al. | 606/232 |

FOREIGN PATENT DOCUMENTS

| | | | | |
|---|---|---|---|---|
| EP | 0 571 686 A1 | 12/1993 | | A61B 2/08 |
| EP | 0 611 557 A2 | 8/1994 | | A61B 2/08 |
| EP | 1 072 234 A2 | 1/2001 | | A61F 2/08 |
| EP | 1 072 237 A1 | 1/2001 | | A61F 2/36 |
| FR | 2777442 | 10/1999 | | A61B 17/04 |
| FR | 2777447 | 10/1999 | | A61B 17/56 |
| JP | 2286468 | 11/1990 | | B62D 1/16 |
| JP | 8-52154 | 2/1996 | | A61B 17/56 |
| JP | 08-206121 | 8/1996 | | A61B 17/04 |
| JP | 11-502437 | 3/1999 | | A61B 17/58 |
| JP | 2000-225118 | 8/2000 | | A61B 17/04 |
| WO | 89/10096 | 11/1989 | | A61B 19/00 |
| WO | 91/06247 | 5/1991 | | A61B 17/00 |
| WO | 95/06439 | 3/1995 | | A61B 17/00 |
| WO | 95/025469 | 9/1995 | | A61B 17/04 |
| WO | 96/28118 | 9/1996 | | A61F 5/00 |
| WO | 97/20522 | 6/1997 | | A61B 2/08 |
| WO | 99/53843 | 10/1999 | | A61B 17/04 |
| WO | 99/53844 | 10/1999 | | A61B 17/04 |
| WO | 02/21997 | 3/2002 | | A61B 17/04 |
| WO | 03/020137 | 3/2003 | | A61B 17/02 |
| WO | 03/049620 | 6/2003 | | A61B 17/04 |
| WO | 11/060437 | 5/2011 | | A61B 17/04 |

OTHER PUBLICATIONS

PCT Search Report and Written Opinion for PCT/US06/21125 6pgs Mailed May 22, 2008.
PCT International Search Report for PCT/US01/21905 3pgs Mailed Jan. 22, 2002.
PCT International Preliminary Examination Report for PCT/US01/21905 3pgs Oct. 17, 2003.
PCT International Search Report for PCT/US01/17689 3pgs Mailed Dec. 19, 2001.
PCT International Preliminary Examination Report for PCT/US01/17689 15pgs Feb. 9, 2003.
PCT International Search Report for PCT/US02/17493 1pg Mailed Mar. 27, 2003.
PCT International Preliminary Examination Report for PCT/US02/17493 4pgs Sep. 8, 2003.
PCT International Search Report for PCT/US02/41018 2pgs Mailed Jun. 5, 2003.
PCT International Preliminary Examination Report for PCT/US02/41018 3pgs Feb. 22, 2004.
PCT International Search Report for PCT/US02/04231 1pg Mailed Aug. 14, 2002.
PCT International Preliminary Examination Report for PCT/US02/04231 3pgs Nov. 13, 2002.
PCT International Search Report for PCT/US03/35695 1 pg Mailed Feb. 14, 2005.
PCT International Preliminary Examination Report for PCT/US03/35695 4pgs Dec. 21, 2005.
EP Partial European Search Report for EP02742470 3pgs Apr. 13, 2004.
EP Supplementary European Search Report for EP02742470 5pgs Jul. 30, 2004.
EP Extended Search Report for EP09162639 4pgs Oct. 28, 2009.
EP Supplementary European Search Report for EP02792506 3pgs Mar. 24, 2010.
UK Search Report for GB 0816111.9 3pgs Dec. 16, 2008.
European Search Report for Ep 02734649 3pgs Jan. 22, 2009.
PCT Search Report and Written Opinion for PCT/US13/33664 10pgs Jun. 14, 2013.
DE Examination Report for DE 102008046561.5 11 pgs Nov. 16, 2012.

* cited by examiner

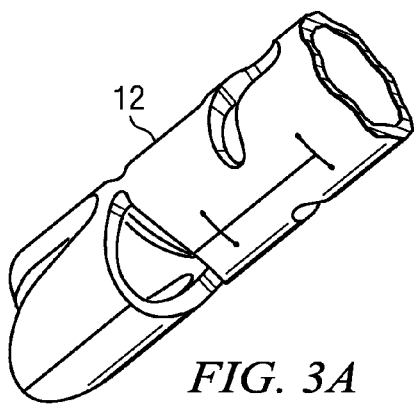
*FIG. 3A*
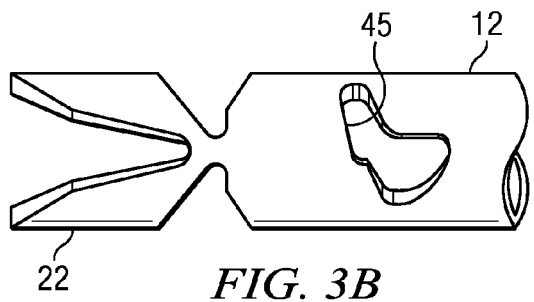
*FIG. 3B*
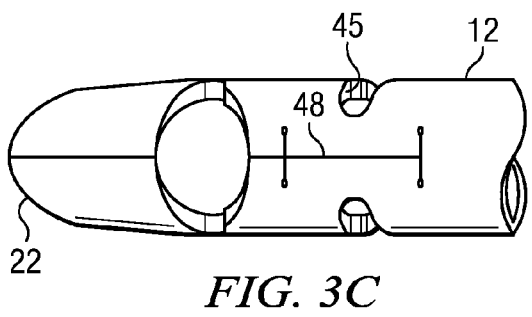
*FIG. 3C*
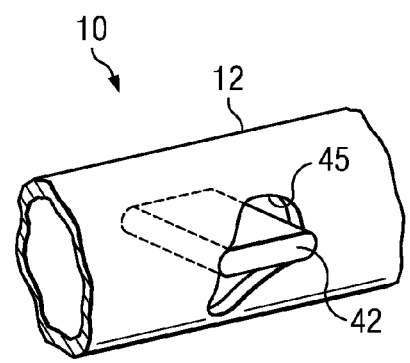
*FIG. 3D*
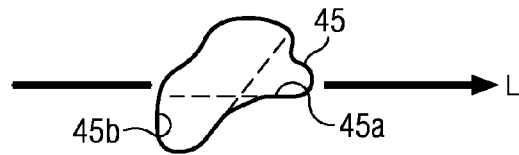
*FIG. 3E*
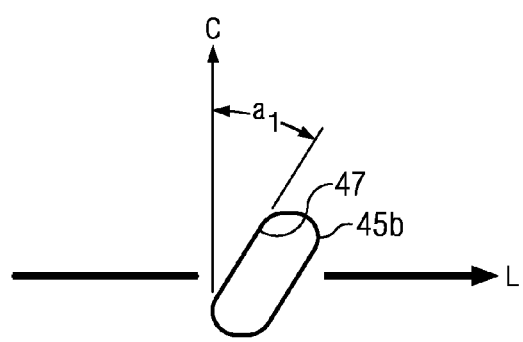
*FIG. 3F*
*FIG. 3G*

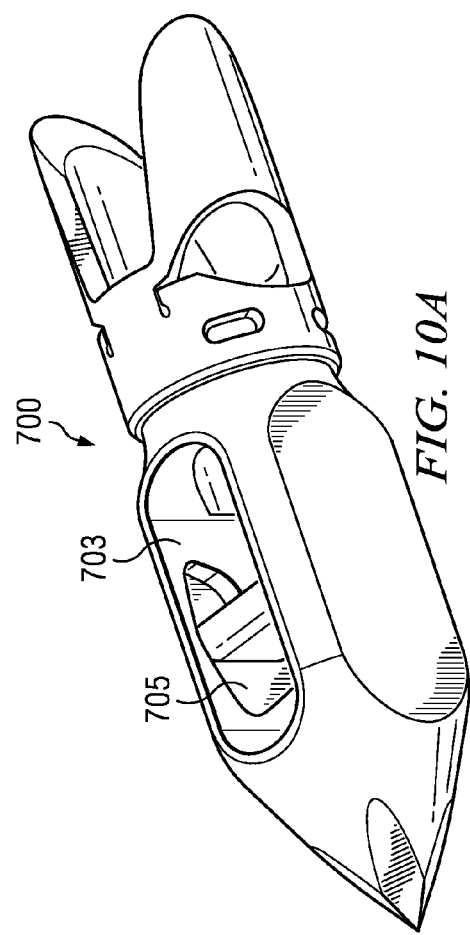
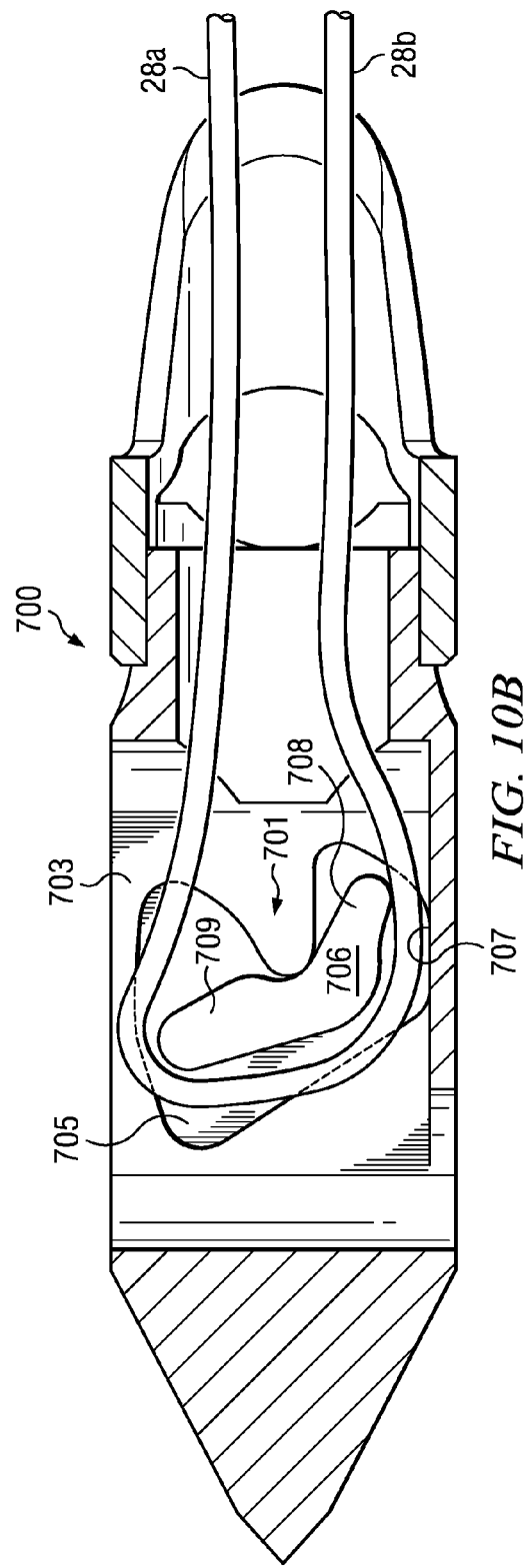
FIG. 10A
FIG. 10B

FREE FLOATING WEDGE SUTURE ANCHOR FOR SOFT TISSUE REPAIR

FIELD OF THE INVENTION

The present invention relates to an apparatus and method for repairing soft tissue regions. More particularly, the present invention relates to an apparatus and method for adjustably affixing torn soft tissues to a region of bone.

BACKGROUND

It is an increasingly common problem for tendons and other soft connective tissues to tear or to detach from associated bone. One type of tear or detachment is a "rotator cuff" tear, wherein the supraspinatus tendon separates from the humerus, causing pain and loss of ability to elevate and rotate the arm. Complete separation of tissue from the bone can occur if the shoulder is subjected to gross trauma, but typically, the tear begins as a small lesion, especially in older patients.

There are various surgical approaches for repair of the rotator cuff, one known as the "classic open" and another as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion.

The mini-open technique differs from the classic approach by working through a smaller incision and splitting rather than detaching the deltoid. Additionally, this procedure is typically performed in conjunction with arthroscopic acromial decompression. Once the deltoid is split, it is refracted to expose the rotator cuff tear. As before, the cuff is debrided, the humeral head is abraded, and the so-called "transosseous tunnels" are "punched" through the bone or suture anchors are inserted. Following the suturing of the rotator cuff to the humeral head, the split deltoid is surgically repaired.

Less invasive arthroscopic techniques continue to be developed in an effort to address the shortcomings of open surgical repair. Working through small trocar portals that minimize disruption of the deltoid muscle, surgeons have been able to reattach the rotator cuff using various suture anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture.

The skill level required to facilitate an entirely arthroscopic repair of the rotator cuff is fairly high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of suture anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed.

There are various suture anchor designs available for use by an orthopedic surgeon for attachment of soft tissues to bone. A number these designs include use of a locking plug which is forced into a cavity of the anchor body to secure the suture therein. Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the suture anchor portion. This action increases the tension in the sutures, and may garrote the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised. Additionally, once the suture is fixed, the suture cannot be adjusted or retensioned. This is a shortcoming of such designs because it is not uncommon for a physician to desire to reposition or adjust the tissue location and suture after the anchor has been set.

A suture anchor that addresses some of the shortcomings mentioned above is shown in FIGS. 1A and 1B. Anchor 1 may include a rotatable or pivoting cam 5 to lock suture 28 within suture anchor 1. Suture leg 28a may be bound or connected to tissue (tissue not shown), and suture leg 28b may be free to be adjusted by the practitioner. In FIG. 1A, the bound suture tension (T1) is minimal as the tissue may not be adjacent the anchor 1, and the practitioner is applying open suture tension (T2) to draw the suture 28 around the cam 5 and draw the tissue attached to bound suture leg 28a closer to the suture anchor 1 and into engagement with the bone. As the bound suture tension (T1) increases, due to the tissue being closer to its target location, T1 may begin to approximate or exceed the open suture tension (T2), and the resulting frictional force $F_{(T1+T2)}$ between the cam 5 and the suture 28 may cause the cam 5 to rotate clockwise, and clamp down and lock or wedge the suture 28 as shown in FIG. 1B. Problematically, as the coefficient of friction between the cam 5 and suture 28 decreases (such as, for example, in low friction environments when certain low friction sutures are used, and/or liquids present), the suture 28 may slip and cam 5 may not rotate or the lock force may not be sufficient, i.e. the lock mechanism may have a tendency to fail. This is undesirable.

Other knotless suture anchors employ axially or translating wedges to actuate the suture lock. For example, U.S. Pat. Nos. 6,520,980 and 6,585,730, both issued to Foerster describe locking wedges which move in an axial direction. The wedge is guided by anchor structures in an axial direction. Frictional forces arise between the contacting surfaces. Consequently, the locking force on the suture is reduced by the frictional forces arising between the wedge surface and the anchor body. It would be desirable to utilize the entire locking force of the wedge to lock the suture without any frictional losses. Frictional losses between the wedge and the anchor body are undesirable because more force is required to lock and unlock the anchor.

Thus, a suture anchor device and method for repairing the rotator cuff or fixing other soft tissues to bone, wherein suture tension can be adjusted, released and conveniently retensioned after it is deployed and locked, and that maintains a strong locking force and functions reliably in a low friction environment is desirable.

It is also desirable that the suture anchor is adapted to lock and unlock the suture when tension is applied to a particular suture leg, and wherein all the force arising from the suture tension is directed to locking and unlocking the suture without frictional losses.

It is also desirable that there is no requirement for the surgeon to tie a knot to attach the suture to the suture anchor, and wherein the procedure associated with the new approach is better for the patient, saves time, is uncomplicated to use, and easily taught to practitioners having skill in the art.

SUMMARY OF THE INVENTION

An anchor device for attaching soft tissue to bone with a suture where the suture is threaded through the anchor device and has a tissue limb of the suture and a free limb of the suture. The anchor device comprises an anchor body wall defining a lumen through the anchor body. A suture locking wedge is movably disposed at least partially within the lumen. The suture locking wedge is in contact with the suture when the suture is threaded through the anchor device and looped around the suture locking wedge such that when a tension force is applied to the tissue limb of the suture, the suture locking wedge is urged into a first position in which the suture is compressed between the suture locking wedge and a first contact location of the anchor body. When a second tension force is applied to the free limb of the suture the suture locking wedge is urged away from the first contact location such that the suture is not compressed.

In another embodiment, the suture locking wedge cooperates with the anchor body to move with a first degree of freedom and a second degree of freedom with respect to the lumen. When a first tension force is applied to the tissue limb of the suture the suture locking wedge is urged into a suture locking position in which the suture is compressed between the suture locking wedge and a first contact location of the anchor body. When a second tension force is applied to the free limb of the suture the suture locking wedge is urged away from the first contact location such that the suture is not compressed and can slide freely around the suture locking wedge.

In another embodiment, the first degree of freedom is rotation and the second degree of freedom is translation. The rotation may be about an axis perpendicular to a longitudinal axis of the suture anchor device. The translation may be in a direction parallel to the longitudinal axis.

In another embodiment, the anchor device further comprises a gap between the suture locking wedge and the lumen such that the suture locking wedge remains substantially free floating when not in the suture locking position.

In another embodiment, the anchor body further comprises a bone fixation structure for securing the anchor device in the bone wherein the bone fixation structure is selected from the group consisting of threads, ridges, barbs, and wings.

In another embodiment, the suture locking wedge comprises a first arm and a second arm, the first arm having a different length than the second arm.

In another embodiment, an anchor device for attaching soft tissue to bone with a suture includes an anchor body comprising a lumen, wherein inner walls which define the lumen comprise at least one window. The anchor device also includes a suture locking wedge movably disposed within the lumen. The suture locking wedge is cooperatively engaged with the window of the anchor body such that the suture locking wedge is movable between a first position and a second position such that when a tension force is applied to the tissue limb of the suture, the suture locking wedge is urged into the first position in which the suture is compressed between the suture locking wedge and a first contact location of the body. When a second tension force is applied to the free limb of the suture the suture locking wedge is urged away from the first contact location such that the suture is not compressed.

In another embodiment, the suture locking wedge has at least one extension member extending laterally from an edge of the suture locking wedge and sized to interface with the window. The at least one extension member may comprise a plurality of pins.

In another embodiment, the suture locking wedge has two substantially planar surfaces which contact the suture. In another embodiment, the suture locking wedge has a uniform height or thickness. The suture locking wedge may have a height that is less than or equal to ½ the diameter of the suture.

In another embodiment, the suture anchor has an elastic or deformable portion. The suture locking wedge may comprise an elastic section which deforms when the suture locking wedge is placed in the first position. In one embodiment the anchor body comprises a slit or cut allowing deformation. The anchor device may further comprise a flexible tether extending between the suture locking wedge and the body.

In another embodiment, the window comprises a plurality of regions. The plurality of regions may include a first region corresponding to the suture locking wedge in the first position and a second region overlapping with the first region and corresponding to the suture locking wedge in the second position. The first region may have a trapezoidal shape.

The window may be covered or uncovered. In one embodiment, the widow is open and uncovered.

In another embodiment, the first region comprises a first distal flat section which forms a first suture locking wedge angle with a radial axis of the anchor device, and the first suture locking wedge angle ranges from 15 to 30 degrees.

In another embodiment, the second region comprises a second distal flat section which forms a second suture locking wedge angle with the radial axis of the anchor device, and the second suture locking wedge angle ranges from 5 to 15 degrees less than the first suture locking wedge angle. In another embodiment, the second suture locking wedge angle is about 15 degrees.

In another embodiment, the suture locking wedge has a shape such that when the suture locking wedge is urged into the first position, the suture locking wedge compresses the suture at a second contact location of the anchor body in addition to the first contact location. In one embodiment, the first contact location and the second contact location are on opposite walls of the lumen.

In another embodiment, the anchor device comprises only two discrete parts not including the suture.

In another embodiment, a method for securing soft tissue to bone comprises: (a) securing a first limb of a length of suture to the soft tissue to be attached to the bone; (b) extending the length of suture into an anchor body and looping the length of suture around a suture locking member movably disposed within the anchor body and such that a second limb of the suture extends from the anchor body; (c) fixing the anchor body within the bone; (d) applying a first tension on the second limb of the length of suture such that the length of suture slides around the suture locking member so as to move the first limb of the suture and the soft tissue towards the anchor body and until a second tension on the first limb of the suture arises from the soft tissue; and (e) releasing the second limb, thereby halting the application of the first tension on the second limb such that the second tension on the first limb of the suture causes the suture locking member to move from the unlocked position to the locked position, thereby compressing the length of suture between the suture locking member and the anchor body.

The method may further comprise manually drawing on the first limb to increase an amount of compression on the length of suture between the suture locking member and the anchor body.

The method may further comprise releasing the suture from being compressed. Releasing may be performed by applying a third tension to the second or free limb of the suture thereby causing the suture locking member to rotate and translate from the locked position to the unlocked position. Additionally, after the step of releasing, the method may further comprise retensioning the suture by drawing on the second or free limb of the suture to reposition the soft tissue relative to the anchor body.

The method may further comprise locking or relocking the suture anchor by manually applying a fourth tension on the first or tissue bound limb of the suture to manipulate the suture locking member into the locked position In another embodiment, a method for repairing soft connective tissue with a suture comprises: (a) providing an anchor device, the anchor device comprising an anchor body and a movable suture locking member at least partially disposed within the anchor body, the suture locking member cooperatively engaged within the anchor body to move between a locked position in which a length of the suture is compressed between a first contact surface of the suture locking member and the anchor body, and an unlocked position in which a gap is defined between the first contact surface of the suture locking member and the anchor body such that the length of suture is not substantially compressed between the suture locking member and the anchor body; (b) securing a first limb of the suture to a first tissue section; (c) extending the length of suture in the anchor body and around the suture locking member such that a second limb of the suture extends therefrom; (d) embedding the anchor body in a second tissue section; (e) approximating the first tissue section towards the second tissue section by applying a first tension force to the second limb of the suture so as to slide the length of suture around the suture locking member thereby creating a second tension force on the first limb; and (f) adjusting the first tension to be less than the second tension thereby causing the suture locking member to move until the suture locking member is seated in the suture locking position, thereby compressing the length of suture. In one embodiment, the step of adjusting the first tension to be less than the second tension causes the suture locking member to move by rotating and translating.

In another embodiment, the step of embedding the anchor body in a second tissue section is performed by embedding the anchor body in a bone.

In another embodiment, the step of adjusting the first tension to be less than the second tension is performed by applying (or increasing) the second tension force to the first (or tissue) limb of the suture. The step of applying the second tension force to the first limb may be effectuated by hand.

In another embodiment, the adjusting the first tension to be less than the second tension is effectuated by halting the applying a first tension force to the second limb during the approximating step.

In another embodiment, a method for repairing tissue with a suture anchor and a suture, comprises: (a) securing a tissue limb of the suture to a first tissue section; (b) inserting a length of the suture into a lumen of the suture anchor, and looping the length of the suture about a suture locking member movably disposed within the lumen of the suture anchor such that a free limb of the suture exits the lumen proximal end; (c) inserting the suture anchor into a second tissue section; (d) applying a first tension on the free limb of the suture such that the length of suture slides around the suture locking member, drawing the first tissue section towards the suture anchor until a second tension is applied on the tissue limb of the suture from the first tissue section; and (e) halting the applying a first tension on the free limb while the second tension is applied on the tissue limb of the suture to cause the suture locking member to move from a suture unlocked position to a suture locked position, compressing the suture between the suture locking member and the suture anchor. In one embodiment, the halting the applying a first tension on the free limb causes the suture locking member to move by rotating and translating.

In another embodiment, the rotating and translating the suture locking member seats the suture locking member in complimentary engagement with the lumen of the suture anchor to compress the suture in the suture locked position.

In another embodiment, a method for repairing soft tissue with a suture anchor and a suture comprises: (a) fixing the suture anchor in a bone; (b) applying a first tension on the free first limb of the suture such that the length of suture slides around the suture locking member, drawing the soft tissue towards the suture anchor until a second tension is applied on the second limb of the suture from the soft tissue; and (c) moving in two degrees of freedom the suture locking member from a suture unlocked position to a suture locked position, thereby compressing the suture between the suture locking member and the suture anchor. In one embodiment, the moving is effectuated by pausing the applying the first tension on the first limb of the suture while the second tension is applied on the second limb of the suture.

In another embodiment, the moving comprises moving in a translational, rotational, angular, non-linear direction, or combination thereof.

In another embodiment, the step of applying a first tension on the free first limb of the suture is carried out until the soft tissue is moved within a threshold distance from the anchor body, such that the second tension arises on the second limb from the soft tissue. The threshold distance may range from 2 to 8 mm. or, in some embodiments, from 3 to 6 mm.

In another embodiment, a method for repairing a soft tissue comprises: (a) providing a plurality of anchor bodies each comprising a suture locking wedge movably disposed therein, the plurality of anchor bodies including a first anchor body and a last anchor body; (b) securing a first limb of a length of suture to the first tissue section; (c) threading the length of suture through each anchor body of the plurality of anchor bodies until the suture is looped around the suture locking wedge of the last anchor body forming an intermediate limb of suture extending into the last anchor body, and a free limb of suture extending from the last anchor body, and such that a sequence of anchor bodies is defined with the suture extending from the first anchor body to the last anchor body; (d) fixing the plurality of anchor bodies in the soft tissue such that the suture length extending between two sequential anchor bodies spans the region; (e) decreasing the size of the region by applying a first tension to the free limb of the suture so as to move at least one of the first tissue section and second tissue section of soft tissue towards the other tissue section; and (f) locking the suture in the last anchor body by moving the suture locking wedge to a suture locking position wherein the moving is effectuated by application of a second tension on the intermediate limb of the suture.

In one embodiment, the region comprises a tear, and decreasing the size of the region comprises closing the tear. The soft tissue may comprise meniscus.

In another embodiment, the step of providing a plurality of anchor bodies comprises providing at least 5 anchor bodies.

In another embodiment, the region does not comprise a tear and the method comprises tightening or plicating the soft tissue. In another embodiment, the soft tissue comprises capsular tissue.

In another embodiment, moving the suture locking wedge is effectuated by pulling on the intermediate limb of the suture by hand.

In another embodiment, moving the suture locking wedge is effectuated by halting applying the first tension to the free limb.

In another embodiment, the step of moving the suture locking wedge comprises rotating an elongate locking arm extending from the suture locking wedge to compress the length of suture between a first contact location of the suture locking wedge and the last anchor body.

In another embodiment, the step of moving the suture locking wedge comprises rotating and translating the suture locking wedge.

In another embodiment, the step of moving the suture locking wedge comprises moving the suture locking wedge in an angular and translational dimension to the first suture locking position.

In another embodiment, the step of moving the suture locking wedge comprises loading the suture locking wedge in the first suture locking position with a biasing member in the last anchor body.

BRIEF DESCRIPTION OF THE DRAWINGS

FIGS. 3A, 3B, and 3C show partial perspective, side, and top views respectively of a suture anchor body prior to being deployed;

FIG. 3D shows a partial perspective view of a suture anchor including a suture locking wedge in an unlocked configuration;

FIGS. 3E-3G show enlarged views of various regions of a window in a suture anchor body;

FIGS. 10A and 10B show another suture anchor including a suture locking cam, an anchor body, and a nest or groove therein;

DETAILED DESCRIPTION

Figure 1A:
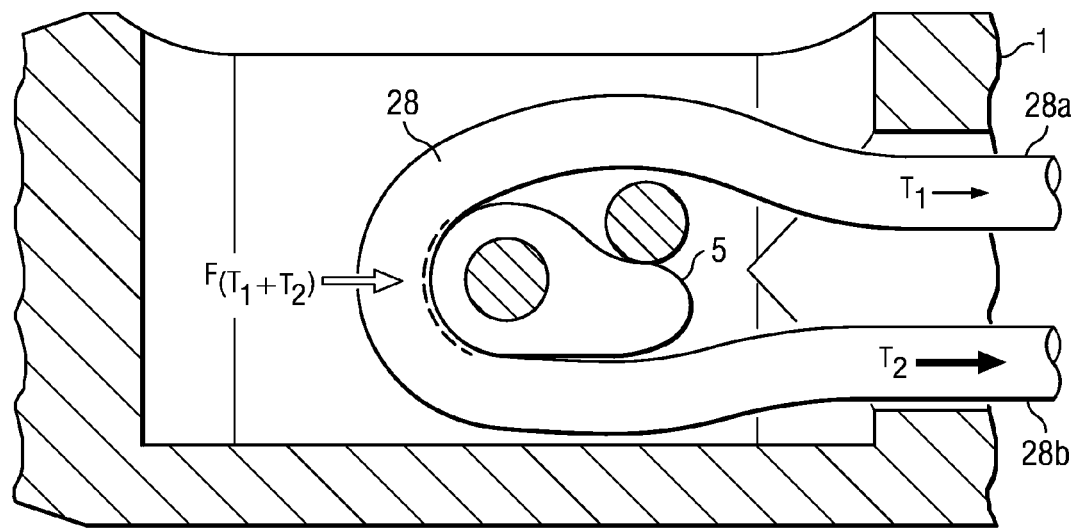
FIGS. 1A and 1B show a partial cross section of a suture anchor having a pinned cam, in an open and locked position respectively.
Figure 1B:
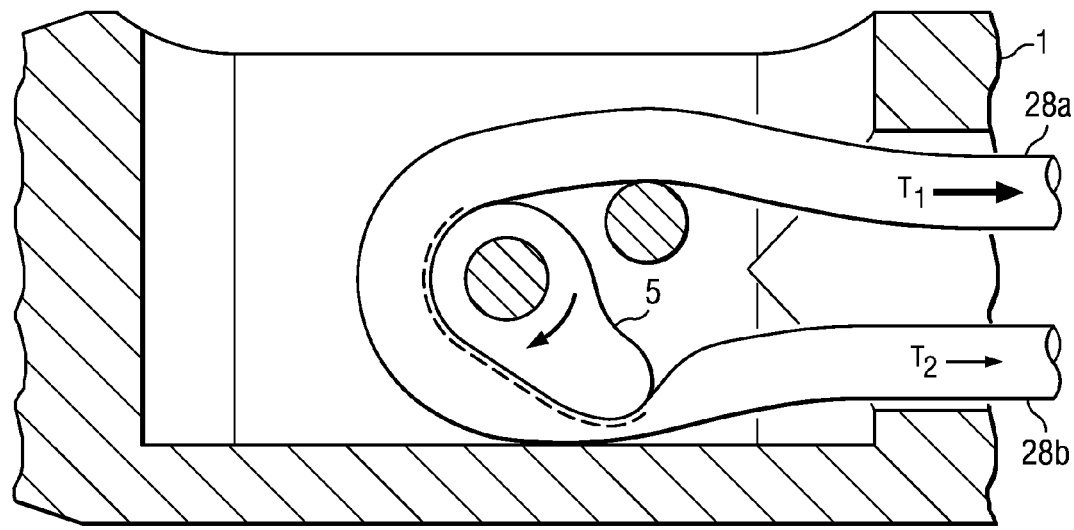

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

The following co-pending patent applications, which are being submitted contemporaneously with the present application, are incorporated by reference in their entirety: U.S. Ser. No. 13/359,631, entitled "ROTATING LOCKING MEMBER SUTURE ANCHOR AND METHOD FOR SOFT TISSUE REPAIR"; U.S. Ser. No. 13/359,673, entitled "RESTRICTED WEDGE SUTURE ANCHOR AND METHOD FOR SOFT TISSUE REPAIR"; U.S. Ser. No. 13/359,826, entitled "BIASED WEDGE SUTURE ANCHOR AND METHOD FOR SOFT TISSUE REPAIR"; U.S. Ser. No. 13/359,891, entitled "METHOD FOR SOFT TISSUE REPAIR WITH FREE FLOATING SUTURE LOCKING MEMBER", all of which are filed on the same date as the present application, and all of which are commonly assigned to ArthroCare Corporation.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

The present invention provides an improved knotless suture anchor apparatus for anchoring a length of suture with respect to a bone structure. In an exemplary embodiment described herein, the apparatus is used to anchor a length of suture to the humeral bone of the human shoulder. The length of suture is desirably looped through soft tissue, such as a rotator cuff tendon, to approximate and fix the soft tissue with respect to the bone structure. It should be understood, however, that the suture anchor apparatus may be utilized to secure a length of suture to anatomies other than in a bone structure. In this regard, the preferred apparatus includes an anchor body within which the length of suture may be adjusted freely and then anchored or secured without knots. If the anchor body is to be implanted within a body tissue, structure on the anchor's exterior may be provided for securing it therein. In a preferred embodiment, the anchor body is inserted within a bone structure, and a pair of wings are deployed from the exterior of the anchor body to hold it within the cavity.

As mentioned above, the present invention is particularly well-suited for repairing rotator cuff injuries by re-attaching the rotator cuff tendon to the outside of the humeral head. Embodiments of the present invention permit minimally invasive surgeries on such injuries and greatly facilitate rapid and secure fixation of the rotator cuff tendon to the humeral head. However, it should be understood that the same principles described herein apply to the repair of other injuries in which soft tissue is to be re-attached to a bone structure or other tissue region.

Embodiments of the present invention permit the user to insert at least one anchor into bone independently of any other anchor, lock an anchor in the bone, allow the user to subsequently tension or loosen a length of suture or wire between the anchors or between the anchor and soft tissue, to affix the soft tissue, immobilize the suture or wire, release and retension the suture, and then disassociate the inserter assembly from the at least one anchor, leaving the at least one anchor and the soft tissue repaired. Such an anchor inserter assembly may preferably eliminate the need to separately pass suture or wire, eliminate the need to tie knots, allow the procedure to be performed without the need to move an arthroscope from an articular side to a bursal side of the cuff, and by virtue of the small diameter of the anchor implants, reduce the size of the hole placed in any tissue, if passing the implant through.

Anchor Structure Overview

Figure 2A:
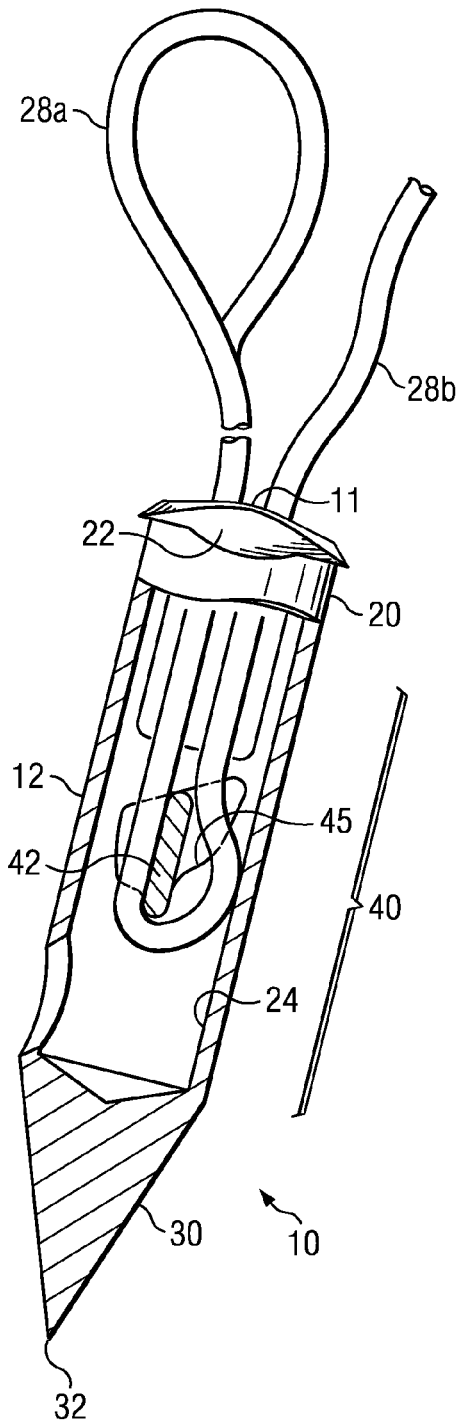
FIGS. 2A and 2B show a cross section of another suture anchor with a free floating suture locking wedge in an open and locked position respectively.
Figure 2B:
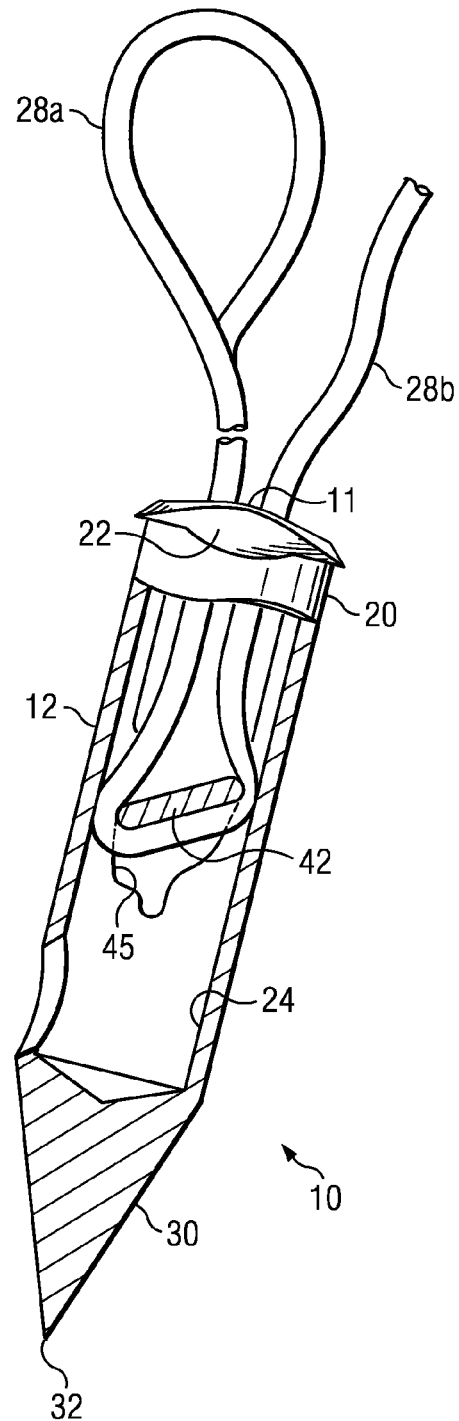

FIGS. 2A and 2B illustrate a suture anchor device 10 including a body 12 which includes a cavity or lumen 24, and a second component, namely, suture locking wedge 42 which is positioned within the lumen 24 of the outer anchor body. The suture locking wedge 42 is adapted to movably cooperate with the anchor body 12 to lock and release a suture 28 by compressing the suture between the anchor components. In particular, anchor body 12 includes a window or slot 45 which allows the suture locking wedge to move from an unlocked open configuration to a locked configuration as will be discussed in more detail herein.

In the embodiment shown in FIGS. 2A and 2B, the lumen 24 commences at a proximal aperture or opening 11, and extends distally along the longitudinal axis of the anchor body 12. The axial lumen 24 is shown as being substantially cylindrical or tubular. However, the shape of the lumen or cavity may vary.

At least one suture 28 which includes at least one bound leg 28a is shown threaded through the opening 11 and extends distally through the lumen 24, around the suture locking member or wedge 42, and may subsequently be redirected proximally back through the lumen 24 and out of opening 11 to result in a free leg 28b. The bound side or leg 28a is considered bound because in practice, this leg, limb, or end of the suture is "bound" to the soft or connective tissues to be attached to the target tissue such as bone by virtue of passing the sutures through the connective or soft tissues using conventional suturing techniques known in the art. The free side or leg 28b is considered "free" because the surgeon or practitioner, in practice, has control over this leg, limb, or end of the suture with his or her hands or appropriate instrumentation.

Suture Locking Wedge

The suture locking wedge 42 is shown being movable within the lumen 24 of the anchor body. The suture locking wedge 42 is free to move linearly, angularly, and to rotate within the lumen. A window 45 cooperates with lateral edges of the suture locking wedge 42 to allow movement in multiple degrees of freedom yet maintain the suture locking wedge within the lumen of the anchor. In a sense, the suture locking wedge is free floating.

In a first or open configuration as shown in FIG. 2A, suture locking wedge 42 is operable to allow suture free leg 28b to be pulled so that the suture may slide freely around suture locking wedge 42 and into, out of, and through suture locking portion 40 so as to pull soft tissue attached to the bound leg 28a closer to suture anchor 10. As the tissue is pulled closer to the anchor, a tension force arises on the tissue bound leg 28a. Tension may also arise by the surgeon pulling on the tissue bound leg 28a. Once a sufficient amount of tension is present on the bound leg 28a, the surgeon may adjust (e.g., release, reduce or halt) the tension on the free limb 28b so as to cause the suture locking wedge 42 to translate and rotate, and to thereby lock the suture 28 against a portion of the anchor body 12.

The shape of the suture locking wedge may vary. In FIG. 2A, the suture locking wedge is shown as a simple plate 42 having two opposing substantially planar surfaces. The suture locking wedge need not have one side or edge thicker than another. Indeed, the suture locking wedge may have, but need not be limited to, a cuboid-like shape. Non-limiting examples of cross sectional shapes of the suture locking wedge include square, rectangle, trapezoidal, oval, arcuate, triangular, and parallelogram.

Suture locking wedge 42 may preferably have a smooth surface, and more specifically, a smooth distal surface to allow for easy suture sliding around the suture locking wedge surface during use. Additionally, the suture locking wedge 42 may have an elongate nest or groove (not shown) to provide some limitation to any lateral motion of the suture 28 (i.e. to keep the suture 28 from slipping off the suture locking wedge 42). The suture 28 itself may also preferably comprise a low friction material such as polyester suture to create an overall low friction environment. Examples of sutures include without limitation low friction UHMWPE suture and polyester suture.

The suture locking wedge may be formed of (or comprise) metal, polymer, or some other material. In a preferred embodiment, the wedge is formed from a riGid, relatively low friction material, so as to allow easy sliding of the suture. Additionally, elastic or resilient materials or components may be incorporated into the suture locking wedge and/or the anchor body. As the suture locking wedge is urged into a locked configuration, the elastic component(s) may deform which can increase the clamping force on the suture.

Windows and Slots

With reference to FIGS. 3A-3D, an anchor body 12 is shown having a substantially cylindrical or tubular shape and two windows or slots 45. Preferably, but not necessarily, the windows or slots extend completely through the wall of the anchor. The windows and slots may be open or covered. Construction of the windows or slots may be carried out utilizing various techniques including, for example, machining Preferably, the anchor body is a metal such as stainless steel and the slots are laser cut.

The windows 45 allow the suture locking wedge 42 to freely rotate and translate yet prevent it from escaping from the tube. A tether or strap (not shown) may optionally be connected between the suture locking wedge and the anchor body to prevent the suture locking wedge from exiting the anchor body. The tether may be made of a polymer or metal and serves to maintain the wedge in the lumen. Such a redundancy is an added safeguard. Additional means for holding the suture locking wedge in position or biasing the suture locking wedge are described in U.S. Ser. No. 13/359,826, filed Jan. 27, 2012, and entitled "Biased Wedge Suture Anchor and Method for Soft Tissue Repair".

An enlarged view of a shape of an exemplary window 45 is shown in FIG. 3E. The window 45 includes a plurality of overlapping regions 45a, 45b. The regions correspond to certain positions of the suture locking wedge to lock the suture, and to allow the suture to be drawn or pulled.

FIG. 3F shows region 45a having a trapezoidal (or cap, hat-like) shape. It includes a horizontal portion 46 with respect to the longitudinal axis (L) of the suture anchor. When in an open configuration, the suture locking wedge rests on the horizontal portion 46 of the first region 45a.

Region 45b is shown having a parallelogram-like shape. It also includes at least one substantially flat surface that forms an angle (a1) with a radial or central axis (C) of the suture anchor. Central axis C is perpendicular to the longitudinal axis (L). When the suture is put in tension during locking, the suture locking wedge is manipulated towards this flat surface 47. Further details of the windows, their function, and suture locking are discussed below in connection with FIGS. 4A-4D.

Although not shown in this example, the anchor body 12 may comprise additional openings or apertures. For example, apertures may provide space or room for suture routing. Suture routing, in some instances, requires the suture to be doubled up around a preloaded snare type device (not shown), and pulled through the anchor. More space at the locations along the suture path where the suture turns is desirable. To this end, apertures are positioned at locations along the suture path where the suture changes direction. The apertures are preferably sized to be at least as wide as the suture diameter. However, the shape, size and location of the apertures may vary. When the anchor is loaded with a suture, for example, a portion of the suture 28 may protrude or ride outside of the anchor body. Alternative embodiments may have additional apertures elsewhere on the anchor body such as, for example, on the opposite or inferior side of the anchor body.

Additionally, with reference to FIG. 3C, at least one slit 48 or cut may be added to the anchor body 12. For example, slit may be laser cut into the body. The slit shown in FIG. 3C allows anchor body 12 to deform to some degree when the suture locking wedge and suture are urged into a suture locking configuration as will be discussed in more detail below. Slit provides some elasticity to the anchor.

With reference to FIGS. 2A, 2B, the distal end section 30 of suture anchor 10 may comprise a piercing tip 32 to penetrate soft tissue and be driven into and through tissue and bone. The piercing tip may facilitate the anchor to be pounded or driven into bone with a mallet or hammer-like instrument. Piercing tip 32 may be hollow or solid depending on strength or weight requirements and manufacturing technique. Suture anchor 10 may be preferably fabricated from a metal such as 316L stainless steel, although other materials such as titanium may be used. Alternative embodiments may include a blunted tip for inserting into a prepared bone passage or a threaded or tissue cutting tip.

After the anchor is positioned within the target tissue, the anchor is fixed so as to remain in place. The suture anchor of the present invention may incorporate a number of features or structures to achieve a bone lock including, for example, assuming a larger profile using a variety of anchoring means such as expansion ribs, molybolts, rivets, wings, and other mechanisms. Alternate embodiments may include a threaded, ridged or barbed portion on the outer surface 12 to lock into the wall of the target tissue (not shown). In one embodiment, proximal end 20 may include an anchoring element with two deformable wings 22 that may be permanently or reversibly deformed or outwardly deployable to have a larger profile so as to anchor or fix the suture anchor 10 within the target tissue.

Suture Locking Detail

Figure 4A:
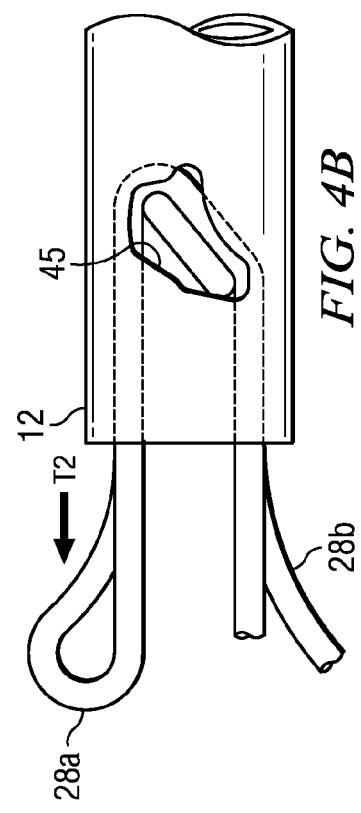
FIGS. 4A-4C show partial side views of a suture anchor and a suture locking wedge in an open, intermediate or transitory, and locked configuration respectively.
Figure 4B:
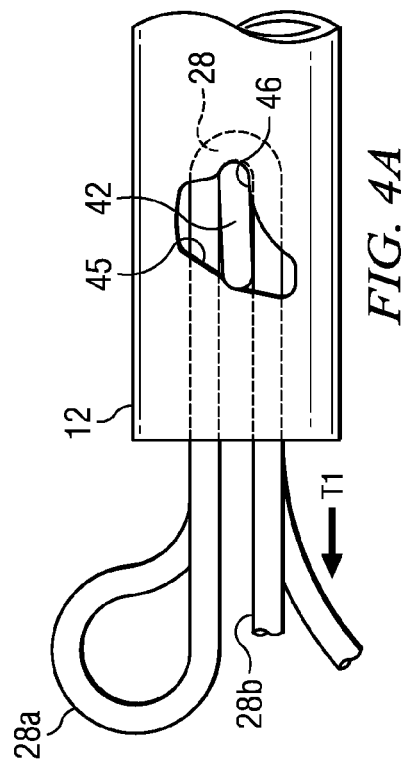
Figure 4C:
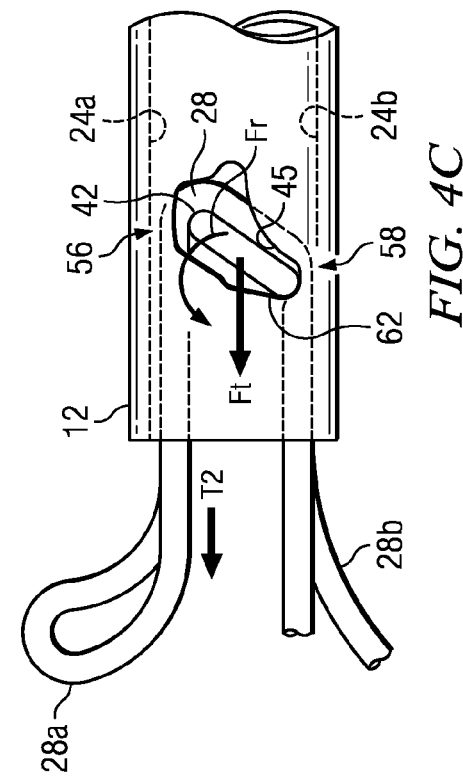

FIGS. 4A-4C are enlarged partial cross sectional views of a suture anchor in an open, intermediate, and a suture locked configuration respectively.

FIG. 4A shows suture locking wedge 42 in its loading position. The suture locking wedge 42 is shown on a horizontal surface, namely, surface 46 of window 45 to provide a position to hold wedge 42 in the suture loading position. Suture loading or routing is often accomplished by doubling the sutures around a pre-loaded snare and pulling the snare through the anchor. This can require double the space for sutures than is required once the suture is snared. Consequently, a relatively large space (or maximum space for a given size anchor outer diameter) is desired between the suture locking wedge surfaces to contact the suture and the walls of the anchor body.

The loading or open configuration allows the suture 28 to slide freely around suture locking wedge 42. A tension (T1) may be applied to suture free end 28b as locking member 42 remains in an open position such that the practitioner may slidingly draw suture 28 around suture locking wedge 42. Consequently, tissue connected to the tissue side or bound leg 28a is positioned or approximated towards the anchor as desired.

As tension (T2) grows on suture leg 28a due to tissue approximation, and the surgeon releases or modifies the tension on the free limb 28b, the suture locking wedge 42 translates and rotates as shown in FIG. 4B until it reaches a final locking position shown in FIG. 4C. The suture anchor design shown in FIGS. 4A-4C provides an area or region through which the suture locking wedge moves as it transitions from a suture loading position to the final suture locking position. The dual use of this area (i.e., for loading and locking) enables the suture locking anchor to be small. Indeed, the height or thickness of the suture locking wedge may be less than or equal to ½ the diameter of the suture. The anchor body may be sized correspondingly small, just large enough to accommodate the suture locking wedge. This configuration thus enables a robust and small suture anchor.

FIG. 4C shows an enlarged partial cross sectional view of a suture anchor wedge 42 in a locked position. In particular, suture locking wedge 42 is shown positioned proximally, compressing suture 28 between edge surfaces of the locking wedge 42, and two suture contacting surfaces 56, 58 of the inner wall 24a, 24b of the anchor body 12.

The suture locking wedge is manipulated into the locked position by drawing on the suture legs. More specifically, a tension (T2) is created on tissue bound end 28a as tissue is approximated to the anchor. A force $F_T$ in the axial direction is applied the suture locking wedge 42 urging it proximally and against the locking surfaces 56, 58. Though FIG. 4C shows pinching the suture at two locations 56, 58, in other embodiments, the suture may be pinched at fewer or more locations. One or more locations may be used to pinch or lock the suture with the wedge.

In addition to the translation force $F_T$, a second type of force or motion is applied to the suture locking wedge 42 when tension (T2) arises in the tissue bound suture leg 28a. Because the suture locking wedge is free to rotate, the suture locking wedge has at least a second degree of freedom (namely, it rotates in addition to translates). A rotation force $F_R$ on the suture locking wedge 42 therefore arises. This force $F_R$ urges the wedge in a counterclockwise direction, and acts to further compress the suture against the suture contacting surfaces as the tissue bound suture leg is placed in tension. As will be discussed in more detail herein, the locking or compression on the suture increases as the tension T2 is increased because of the translation, and rotational forces placed on the suture locking wedge 42.

Figure 4D:
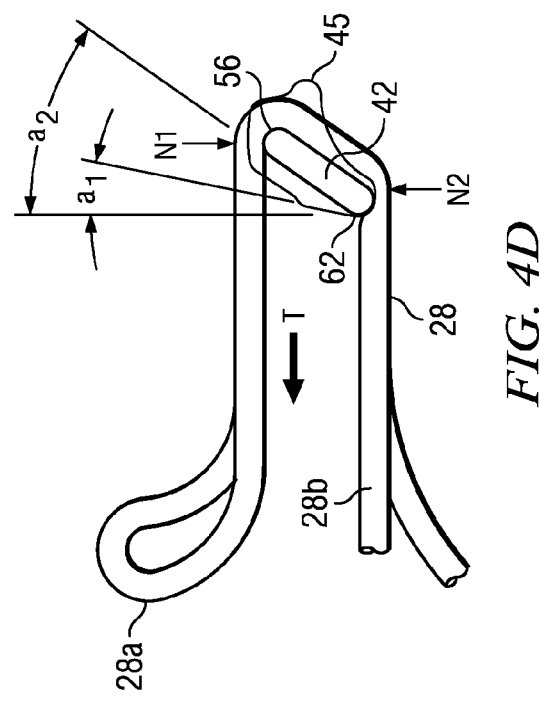
FIG. 4D shows a diagram illustrating various forces on a suture locking wedge arising from tension on a suture.

Without being bound by theory, FIG. 4D is intended to illustrate some of the mechanical dynamics of a suture lock. As shown, a tension T in the tissue side of the suture loop 28a supplies energy in the lock. The energy in the lock can be represented by normal forces at N1 and N2 where (N1+N2)× coefficient of friction=lock force.

It can be seen that N1 and N2 vary with suture locking wedge angles a1 and a2. As a2 increases, N1 and N2 decrease. As a2 decreases, N1 and N2 increase.

At a2 equal to 30 degrees, N1 is estimated to be 173% of T and N2 is estimated to be 105% of T. At a1 equal to 15 degrees, N2 increases to 126% of T. At this point, the lock is at nearly 300% of T. This means the suture will lock if the coefficient of friction is greater than ⅓.

Additionally, at a2 equal to 20 degrees and a1 equal to 15 degrees, the lock is at 535% of T and the suture will lock if the coefficient of friction is greater than about ⅕. Thus, as more and more tension is placed on the lock; the walls of the tube will expand, the suture will compress smaller, and the wedge will rotate to smaller angles enabling it to work even more efficiently.

It is noted that the frictional losses (e.g., frictional loss arising from the suture being drawn around the wedge) has been omitted from the above analysis. However, adding F(loss) would increase suture locking. The frictional properties of the materials involved can be changed by altering surface roughness, treatments, and oxide content. As a1 and a2 get smaller, the ability of the lock to function increases dramatically theoretically approaching infinity. The smaller angles also have a binding affect on the lock which can help the lock function in cyclic loading environments. In one embodiment a2 ranges from 15-30 degrees and a1 is 5-15 degrees less than a2.

Decreasing angles a1, a2, however, can also have adverse effects. For example, the sutures are harder to unlock by pulling on suture tails 28b as angles a1 and a2 become smaller. This is because unlocking is performed by rotating wedge 42 around point 62. This is accomplished by pulling on suture tails 28b and the friction between suture 28 and wedge 42 at 56 grabs the wedge and pulls it about point 62 on slot 45. As this rotation starts, point 62 on slot 45 can lift a little to let the suture pass the other side of wedge 42 as well. The friction at 56 increases as a2 gets larger making this unlocking dynamic easier.

Utilizing a combination of the above described parameters, the suture anchor of the present invention moves the suture locking wedge from the open loading position to a locked configuration. The anchor body cooperates with the suture locking wedge to move the wedge with multiple degrees of freedom. Limiting the points of contact between the suture locking wedge 42 and the window 45 (e.g., to only one point of contact 62) enables most of the tension energy supplied by the suture to be translated into the lock. Consequently, the suture locking wedge of the present invention can apply a greater clamping force than a standard plug or cam having only one degree of freedom. As discussed below, the anchor may be conveniently implanted, tensioned, locked, unlocked, and retensioned as desired.

Anchor Implantation Using Instrument

Figure 5A:
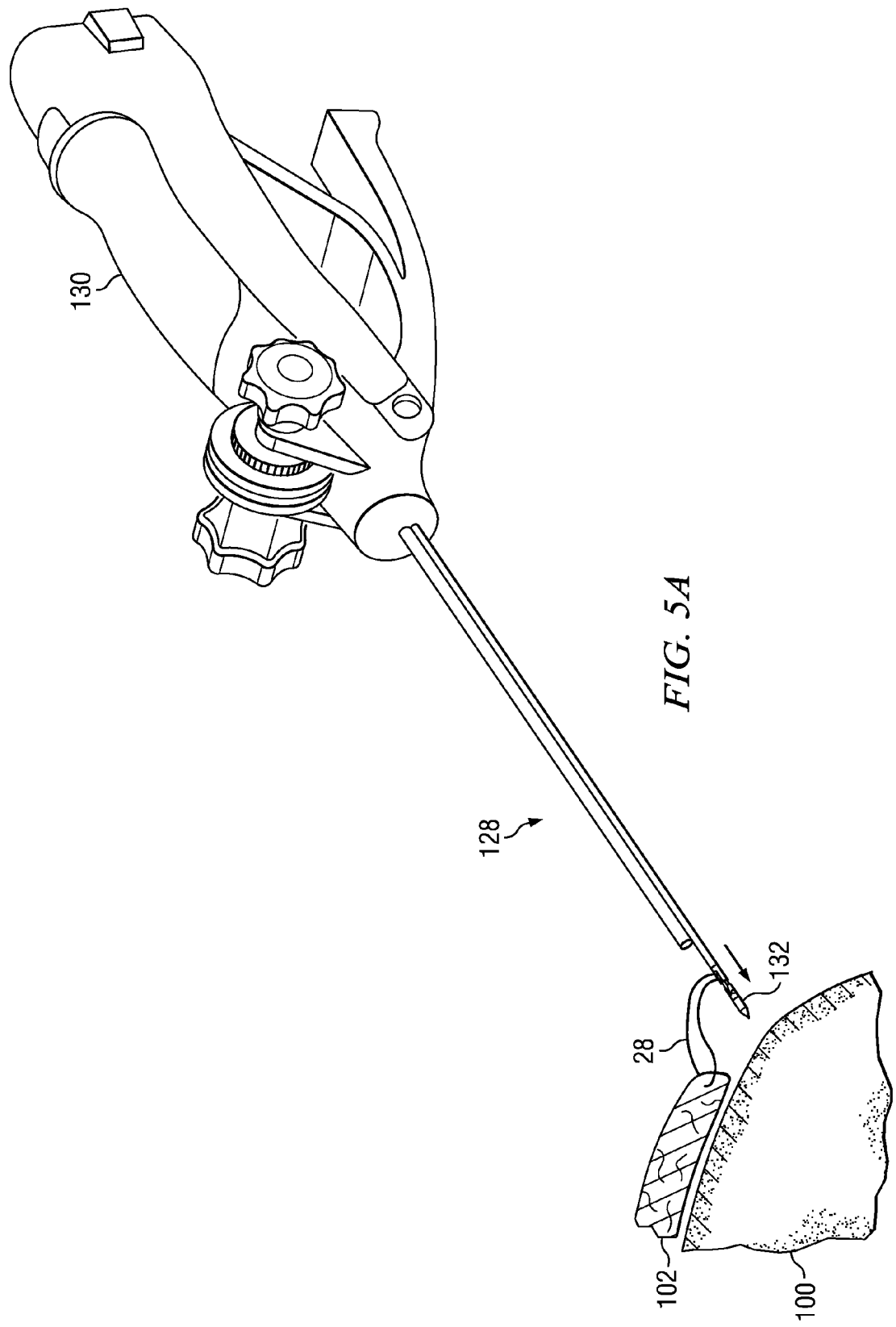
FIGS. 5A-5C show an insertion instrument loaded with a suture anchor, and the steps of inserting and anchoring the suture anchor in a bone.
Figure 5B:
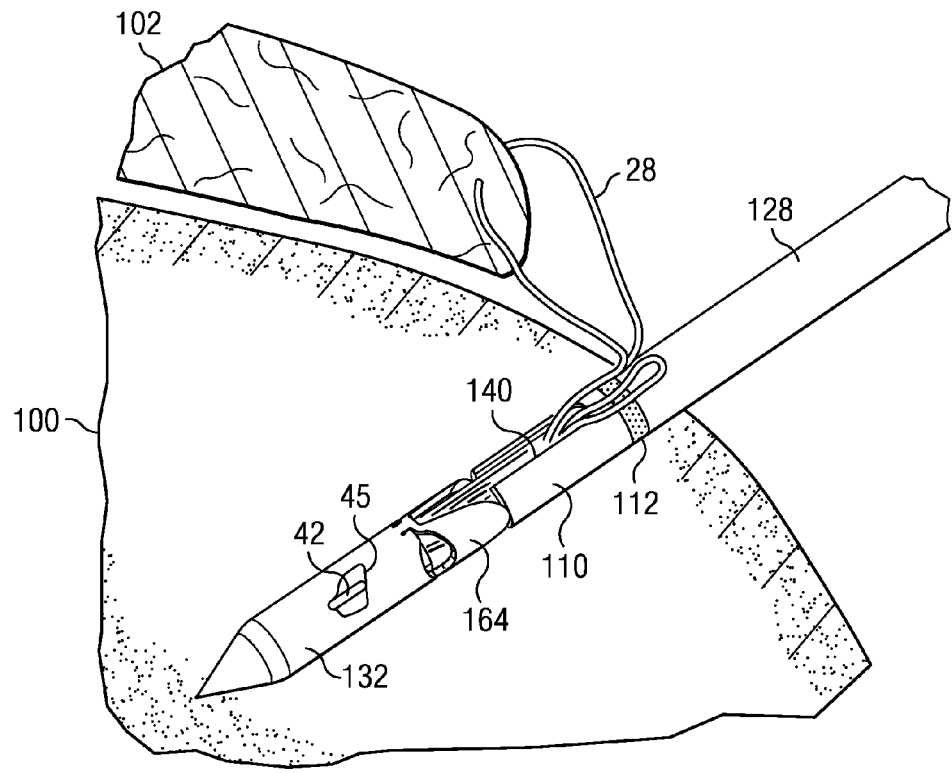
Figure 5C:
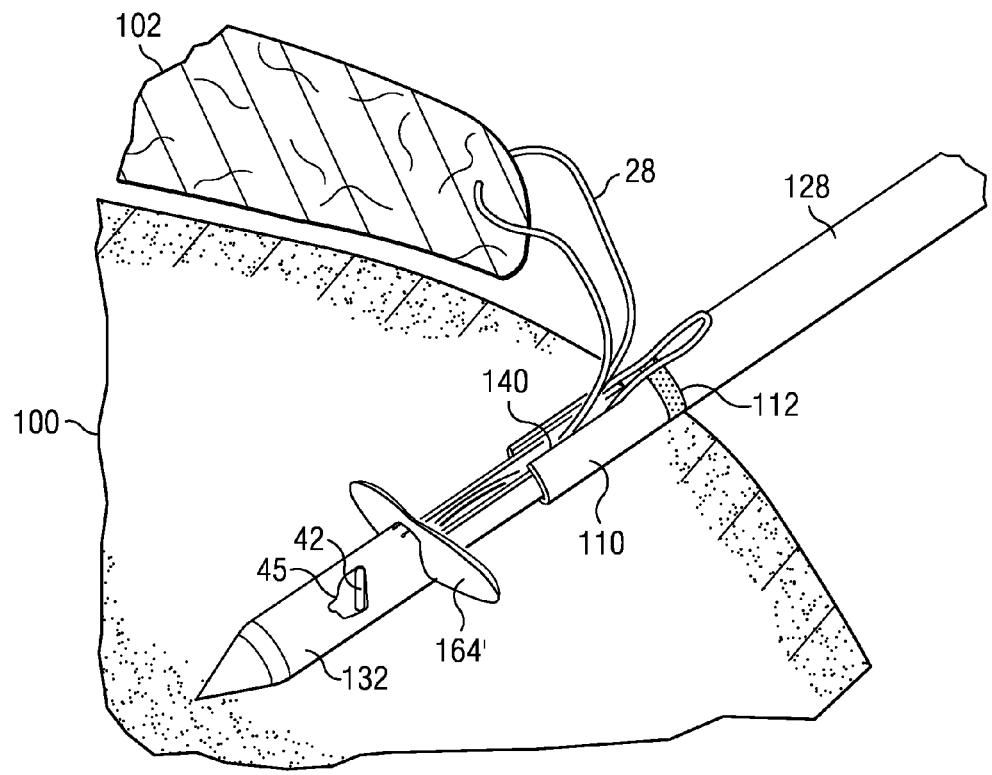

FIGS. 5A-5C illustrate a suture anchor being implanted. As shown, suture 28 may be previously stitched, connected to or looped through tissue 102 and preassembled within anchor 132 (e.g., routed through the anchor using a snare) and instrument 128. The stitching process may be accomplished by any known means, and any known suture stitch may be employed. A stitch is desirably secured so that the suture is not inadvertently separated from the tendon after completion of the repair procedure, necessitating re-entry to the surgical site. In preferred approaches, the suture is attached to the soft tissue using a "mattress stitch," which is well known in the art as being a particularly secure stitch which is unlikely to fail postoperatively.

Anchor 132 may then be brought into contact against the underlying bone region 100 using instrument handle 130. Now with reference to FIG. 5B, the proximal end of the instrument 128 or handle 130 may be tapped, e.g., by using a mallet, to drive the suture anchor 132 into the bone at a depth of, for example, approximately 6 mm. If viewed through an arthroscope, primary anchor 132 may be driven into the underlying bone 100 until an anchor depth indicator 112, e.g., a colored marking or gradation is visible just above or at the bone 100 as a visual indicator to the user that the appropriate depth for anchor insertion has been reached. This may indicate that the anchor wings 164 have been inserted at the correct depth. Instrument 128 may also have lateral aperture or opening 140, located at the distal portion of the instrument but proximal to anchor wings 164, operable to allow passage of suture 28 from tissue 102 into the anchor. Suture 28 may then extend distally from aperture 140 within anchor 132, around a suture locking wedge (not shown) and return proximally within instrument (not shown here) and may connect with a portion of the instrument handle 130, operable for managing the suture 28 during insertion and tensioning.

With suture anchor 132 suitably implanted, the anchor wings 164' may be deployed within the bone 100 using instrument 128, to lock the position of anchor 132 and to prevent or inhibit anchor 132 from being pulled out of bone 100, as shown in FIG. 5C.

Anchor 132 may then be released from instrument 128, which may be achieved by a variety of mechanical means, operable to have a weakness or failure point that fractures or disconnects upon application of a force or torque. For example, instrument 128 may comprise a die or driver 110 that moves relative to the anchoring structure 164 so as to urge the anchoring structure radially outwards. Some methods for this type of release are described in U.S. Pat. No. 6,585,730, which is hereby incorporated by reference in its entirety. Also, it is to be understood that a wide variety of structures may be included with the suture anchor to implant the anchor in bone including without limitation barbs, ridges, threads, etc. Aspects of an instrument and method described in U.S. Patent Application Publication No. 2009/0069823 (which is hereby incorporated by reference in its entirety) may be used to insert and deploy anchor 132. Additionally, the anchor may be implanted in other manners, and without a sophisticated instrument as described above.

Figure 6A:
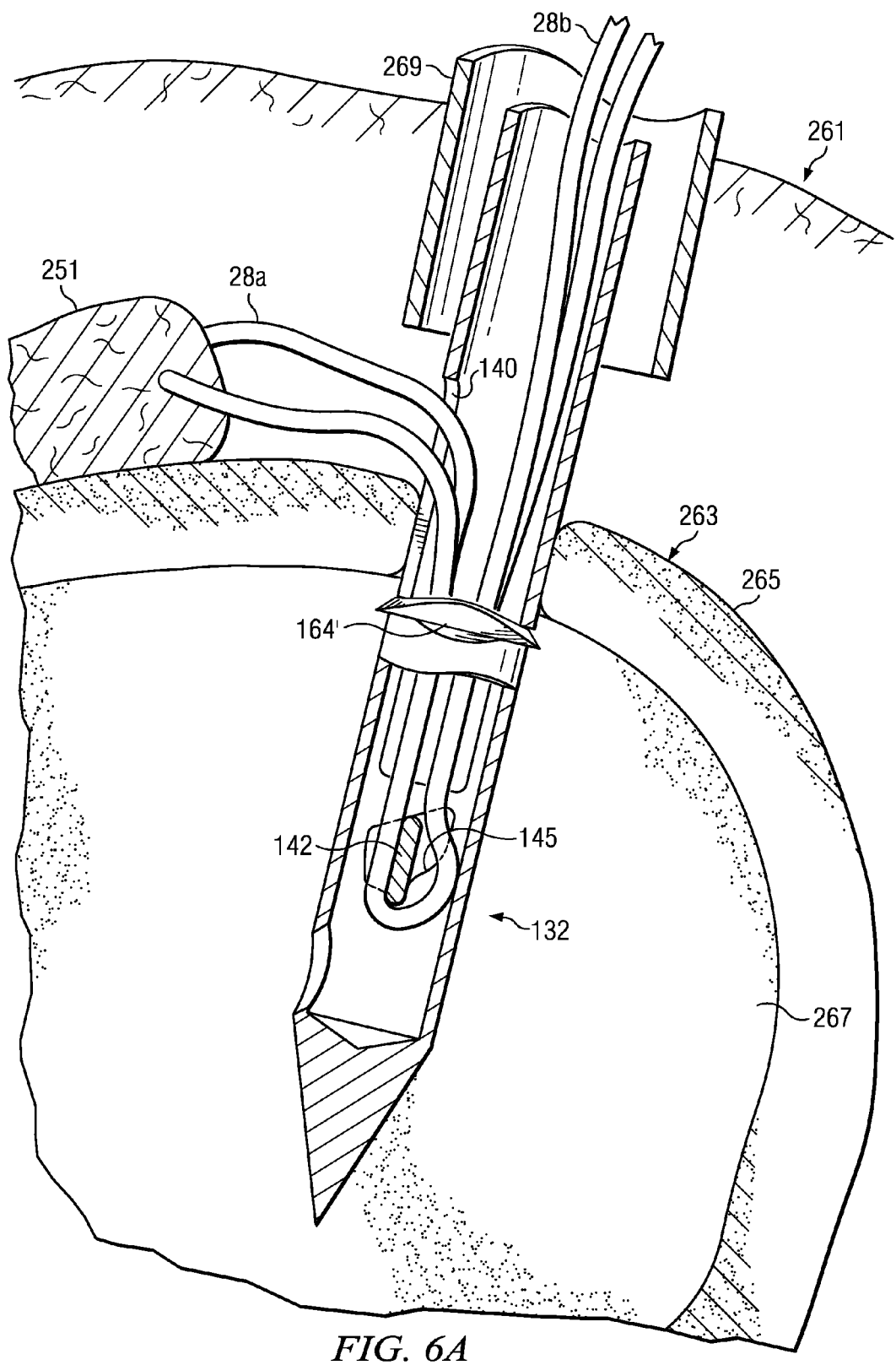
FIGS. 6A and 6B show a suture anchor in rotator cuff tissue in an open suture and locked suture configuration respectively.

FIG. 6A shows a cross section of anchor 132 similar to the anchor described in FIG. 2. Anchor 132 is shown within bone tissue 267 and with anchoring structure 164' deployed in the bone. The bone tissue 267 is that of a shoulder 261, which comprises a humeral head 263, including an outer cortical bone layer 265, which is hard, and inner cancellous bone 267, which is relatively soft. As is typically the case for rotator cuff injuries, in this instance the supraspinatus tendon 251 has become separated from the humeral head 263. It is desirable to reattach the tendon 251 to the humeral head 263. Alternate rotator cuff repair procedures are also discussed in U.S. Pat. No. 6,524,317, and entitled "Method and Apparatus for Attaching Connective Tissues to Bone Using a Knotless Suture Anchoring Device", which is hereby incorporated by reference in its entirety.

To effect the rotator cuff repair, the practitioner may first create an incision in the patient's shoulder 261, into which may be inserted a trocar 269, as shown in FIG. 6A. The trocar 269 permits access to the procedural site for visualization instruments, as well as working instruments, and permits the procedure to be completed arthroscopically. Anchor 132 may then be connected with suture 28 and then inserted according to methods described herein. Insertion to the cortical layer 267 is important to ensure anchoring structure 164' gains good purchase on the bone. Anchoring structure 164' is deployed, at which point the deployment instrument may be disconnected from the anchor 132 as discussed earlier and removed from the site.

Figure 6B:
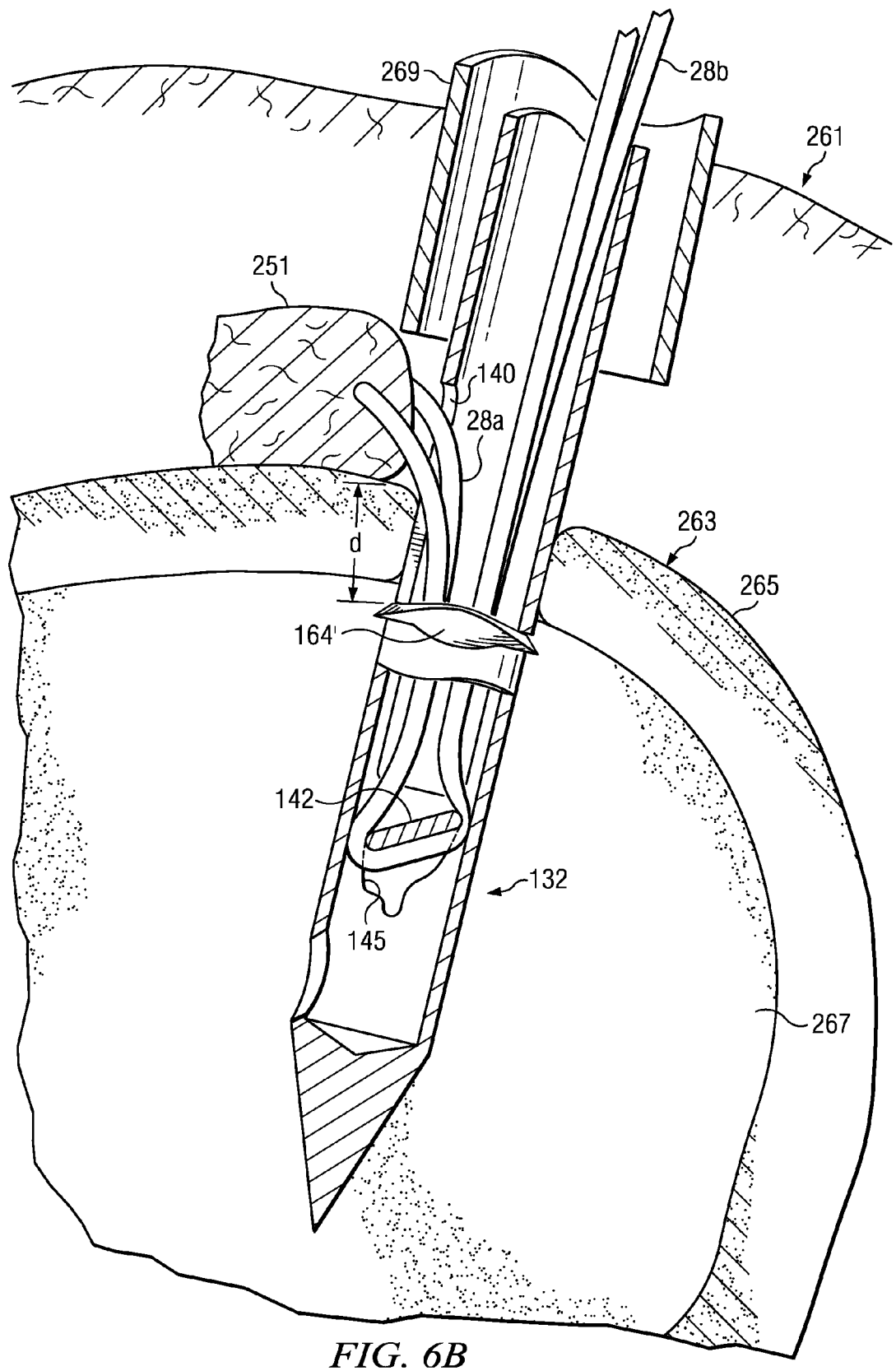

With reference to FIG. 6A, suture locking wedge 142 is shown in an open position, meaning that the suture free end 28b may be freely tensioned or withdrawn proximally to draw tissue 251 to the correct location for reattachment to the bone. As discussed herein, the bound leg or legs 28a of the suture have been connected with the tissue or tendon 251 and may extend through a lateral aperture 140 in the delivery instrument 128 to gain access to the suture anchor 132, about the suture locking wedge 142, until such time as the tendon 251 binding in the bound leg 28a of the suture 28 creates a tension in the suture 28. This will occur when the tendon 251 has been drawn toward the anchor 132 as shown in FIG. 6B, and is itself under appropriate tension for an anatomically proper repair and otherwise snugly situated with respect thereto. Non-limiting examples of threshold distances between the tissue 251 and the proximal end of the anchor range from 2-8 mm and more preferably 3-6 mm. The suture may be drawn by hand, by instrument, or a combination thereof.

Once the tension on the bound limb is present, the practitioner may release or otherwise modify the tension on the free limb so as to allow the tension in the suture bound leg 28a to move the suture locking wedge 142. In the embodiment shown in FIGS. 6A-6B, the suture locking wedge translates, and then rotates within window 145 to the locked position as shown in FIG. 6B.

Reversibility

The suture locking mechanism of the present invention may be unlocked. It is reversible. Retensioning may be possible to permit the continued adjustability of the bound end 28a by applying tensile force to the free end 28b of the suture. This is useful as a surgeon will often find that, during the course of a procedure, after the tendon/soft tissue 251 has been brought into what is believed to be a desired position relative to the bone to which it is being secured, and the suture 28 has been locked into place to retain the tendon in that orientation, a further adjustment is necessary or desired to optimize the outcome.

For example, after the free end 28b has been pulled proximally sufficiently such that a tension is created in the bound end 28a (due to approximation of the tendon 251 to the bone 263), and the suture 28 is locked by the suture locking wedge 142, the bound end 28a is anchored in a fixed position. This ensures that the tendon is not movable relative to the bone after completion of the procedure. However, if the practitioner requires the suture locking wedge to be unlocked, the practitioner may do so by applying sufficient tension on the free end 28b, (possibly also in combination with releasing tension on the bound legs 28a) so as to permit adjustment of the size of the suture loop through the tendon 251, which in turn permits adjustment or fine tuning of the position of the tendon 251 with respect to the bone. The practitioner may make these adjustments by hand or using an instrument.

Once the tendon 251 is adjusted to the desired location, the suture 28 may then be relocked as described above. The free end 28b may be trimmed near the proximal end of the anchor portion 164', and the incision is closed.

Repeated stress or use of the tendon after the surgery may tend to move or dislodge the suture locking wedge. However, the increased clamping force on the suture arising from the suture locking wedge having multiple degrees of freedom (and consequently increased leverage) serves to prevent dislodgement of the suture locking wedge. This is one advantage of the present invention even in low friction environments.

Alternative Embodiments

Figure 7C:
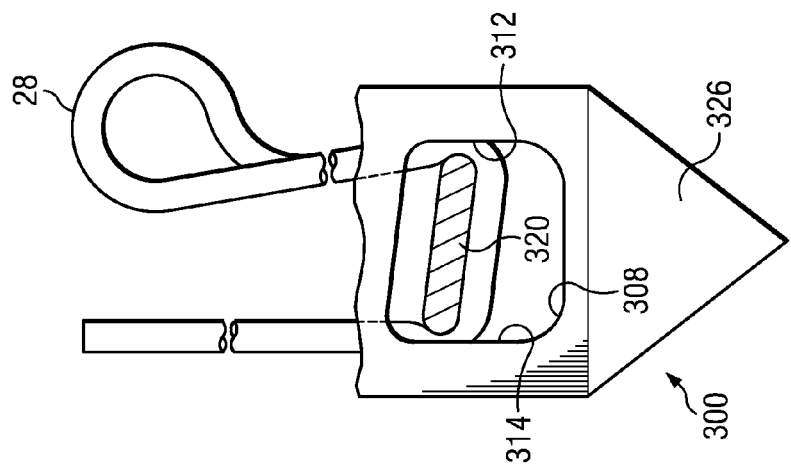
FIGS. 7A-7C show another suture anchor including a suture locking wedge, an anchor body, and a trapezoidal shaped window therein.
Figure 7B:
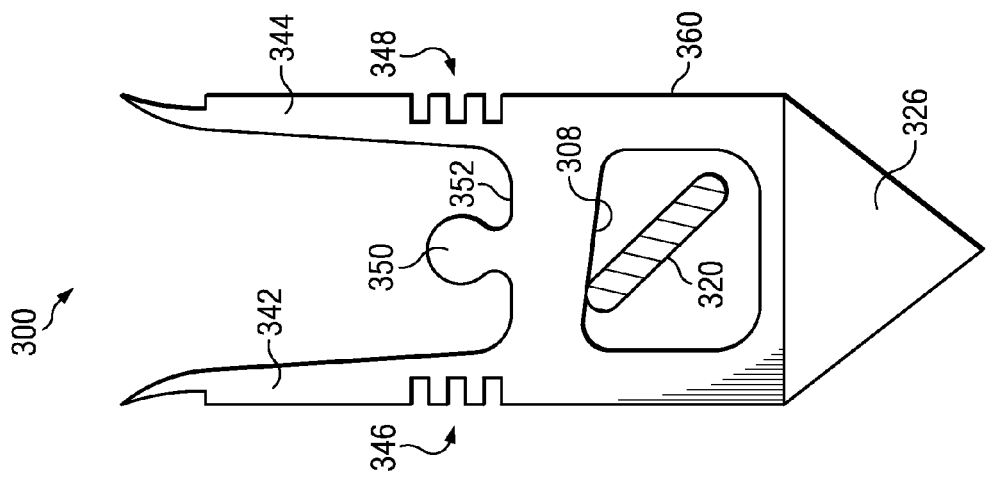
Figure 7A:
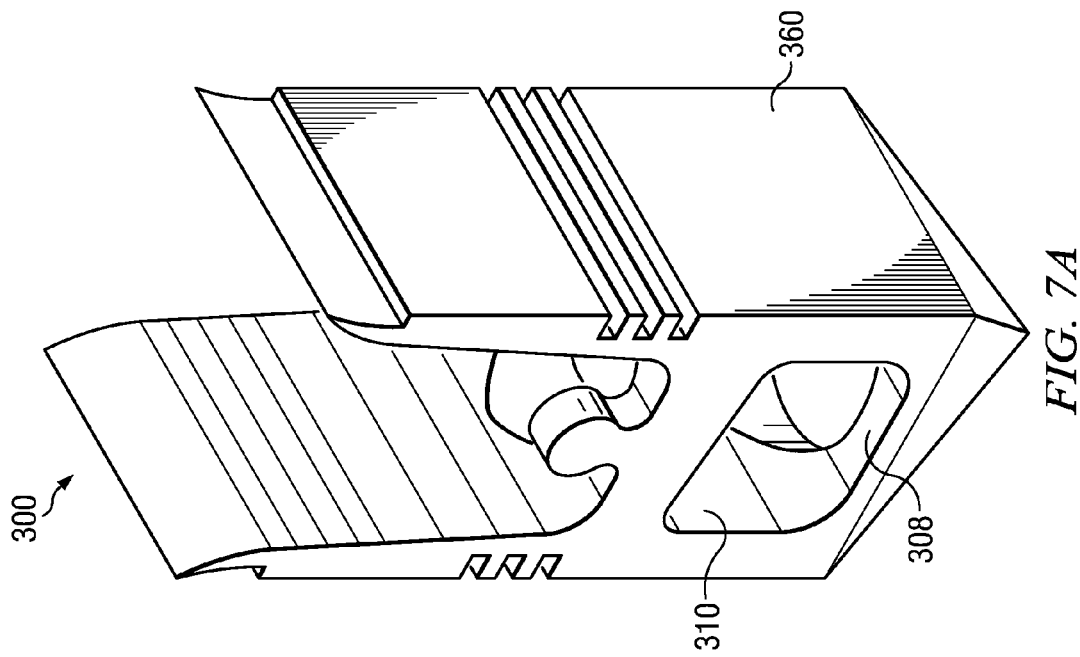
Figure 8B:
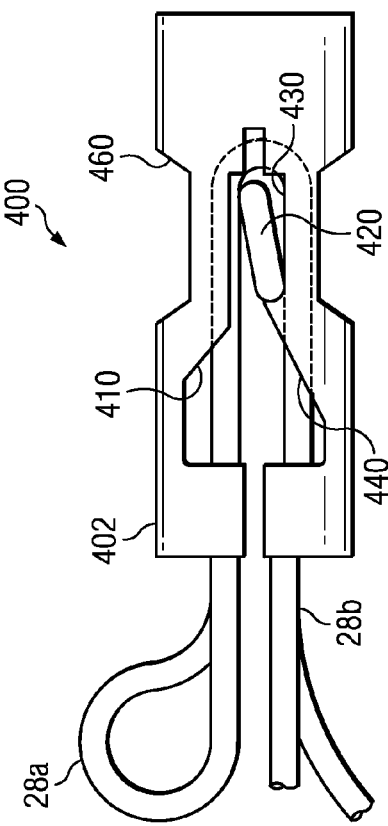
FIGS. 8A-8D show another suture anchor including a suture locking wedge, an anchor body, and a multi-region window therein.
Figure 8A:
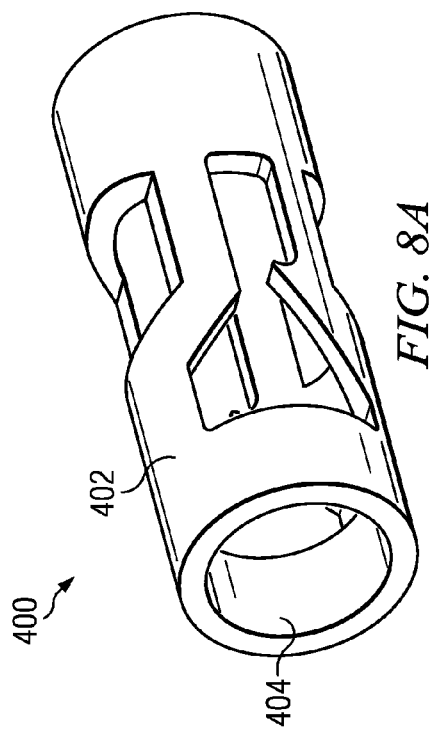
Figure 8D:
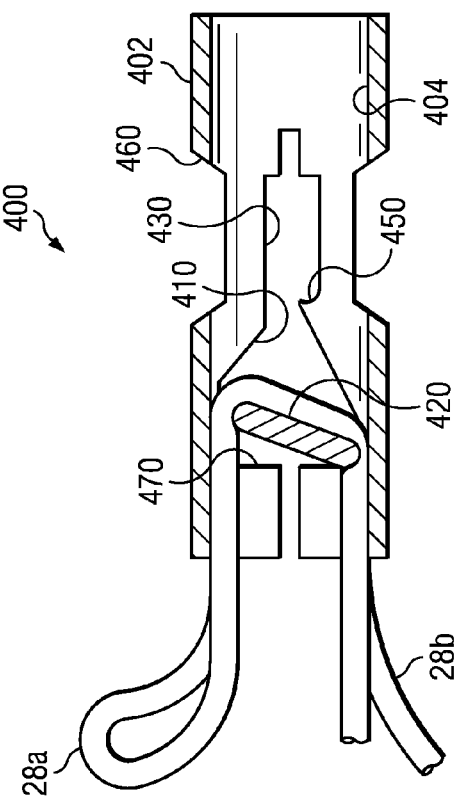
Figure 8C:
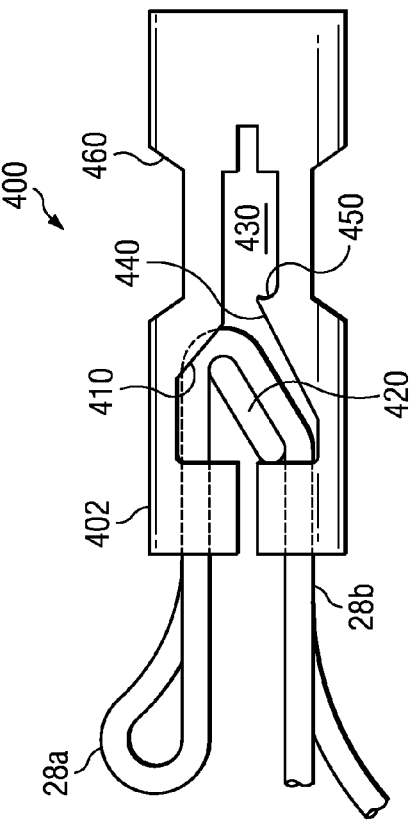

FIGS. 7A-7C show another suture anchor 300. The suture anchor shown in this embodiment has an anchor body and a suture locking wedge 320 movably disposed therein. The anchor body includes an internal lumen 310 having a square cross section.

The suture locking wedge 320, which has a plate like shape, is held in the anchor by a pair of trapezoid-shaped slots 308 present in the anchor body. The suture locking wedge 320 has a lateral portion that extends within groove 308, and the motion of suture locking wedge 320 is restricted or directed by the shape of the slot 308.

When the suture is placed in tension as described above, wedge 320 translates and rotates proximally until it pinches the suture against the internal lumen 310 as shown in FIG. 7C. Suture 28 is shown in FIG. 7C being pinched or compressed at locations 312 and 314.

The suture anchor 300 may be pounded into the bone and fixed therein similar to that described above in connection with FIGS. 5A-5C. In particular, a driving component (not shown) may be releasably attached to feature 350. The driving component may abut surface 352 to drive anchor 300 into the bone.

The anchor may include a sharp trocar tip 326 to pierce the bone. Wings 342 and 344 are deflected by a die member of the instrument (not shown) and pivot at joints 346 and 348 respectively thus driving the wings into the bone. Deflection of the wings into the bone fixes or secures the suture anchor 300 in the bone. The suture may be snared and locked as described above.

FIGS. 8A-8D show another suture anchor 400 having a suture locking wedge 420 movably disposed in an internal lumen 404 of an anchor body 402. The lumen is tubular, having a circular cross section.

The suture locking wedge 420 has lateral edges which engage a window 410 in the anchor body 402. Similar to the suture anchors described above, the suture locking wedge 420 cooperates with the anchor body to allow suture loading, and upon applying tension to the sutures, the wedge is moved into the suture locking position which pinches the suture against an internal surface of the suture anchor.

In the embodiment shown in FIGS. 8A-8D, the window comprises two regions, namely, a rectangular-shaped first region 430 which allows the suture to be loaded or snared, and a second pentagon-shaped region 440 which allows the suture locking wedge to translate and rotate until the suture is compressed against the internal lumen 404, thereby locking the suture.

Though the suture anchor shares some features in common with those described above, the suture loading configuration 430 differs in that the window 430 has a nearly separate, discrete, deep pocket to contain wedge 420 during snaring. This, in combination with aperture 460, provides sufficient space for suture snaring and routing.

The window 410 additionally includes stop feature 450. Stop feature 450 provides additional stability for the wedge during suture routing.

The surface 470 has an angle of about zero degrees. As stated above in connection with FIGS. 4A-4D, this increases the locking force. However, the invention is not so limited. The surface 470 may make other angles with the radial plane.

Figure 9A:
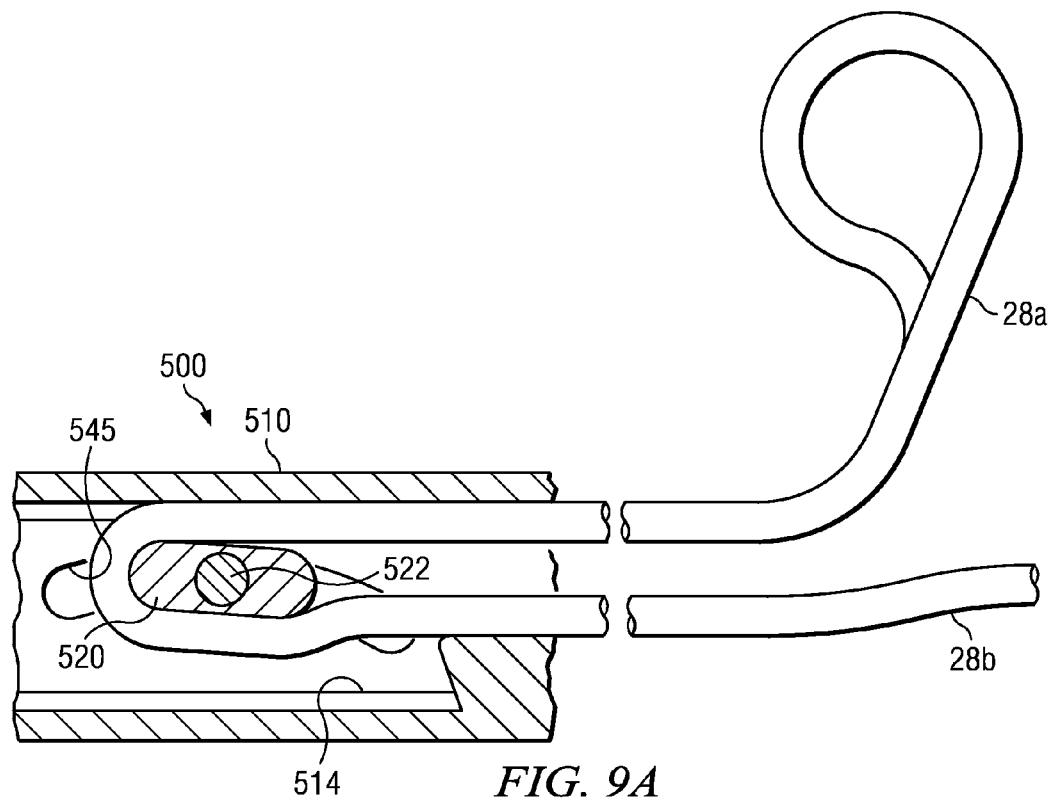
FIGS. 9A and 9B show another suture anchor including a suture locking wedge, an anchor body, and a curved slot therein.
Figure 9B:
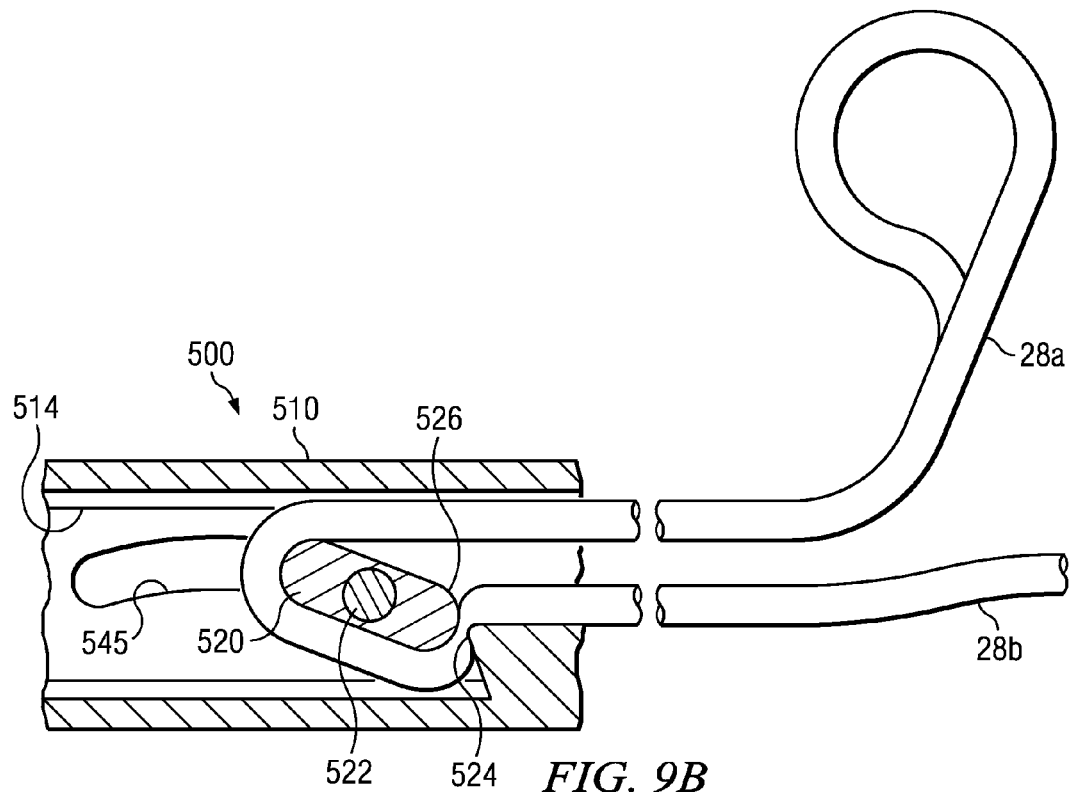

FIGS. 9A and 9B illustrate another suture anchor 500 including a suture locking wedge 520 having multiple degrees of freedom. The suture anchor is shown in an open or unlocked configuration in FIG. 9A, and a suture locked position in FIG. 9B.

With reference to FIG. 9A, the anchor body 510 includes a slot 545 which guides the movement of the wedge 520 along a curved or arcuate path. The wedge engages the slot with a pin 522. Pin 522 is shown extending laterally from the edge of suture locking wedge 520. The pin preferably does not protrude beyond the exterior surface of the anchor body.

In the unlocked or open position shown in FIG. 9A, the suture locking wedge 520 may be held in a near horizontal position. As described above, holding the suture locking wedge in a substantially horizontal or lateral position, in combination with maintaining a large gap or space for the suture to be routed, is desirable. Additionally, although not shown, the anchor body wall 510 may have apertures to provide additional space for the suture to be routed around the suture locking wedge. Portions of the suture may reside outside or outboard of the anchor body. Therefore, the suture need not be confined to the lumen as it is routed around the suture locking wedge.

After the suture anchor is loaded with the suture, or snared, and a tissue is attached to the leg 28a as described above, suture 28b is drawn. As the tissue becomes properly situated with the respect to the anchor and the relative anatomy, a tension force is applied to the suture locking wedge 520.

As the suture applies a force to the suture locking wedge, the suture locking wedge translates axially, and moves angularly along the arcuate path defined by the slot 545. Additionally, because the suture locking wedge is held by only one pin 522, suture locking wedge is free to pivot and rotate about the pin axis. Consequently, the suture locking wedge translates, moves angularly, and rotates to compress the suture against a suture contacting surface 524 of the body 510.

In this embodiment the suture contacting surface 524 is shown being nonparallel to the axis of the lumen. However, the suture contacting surface can be any angle from the axis that is suitable for the degree of locking desired.

Additionally, the combination of the types of motions increases the suture locking force. The reduced number of contact points between the suture locking wedge and the anchor body allows more of the suture compressing force arising from tension on the suture to be directed to compressing the suture and not lost on friction between the anchor components. Additional suture anchor designs having guided wedges are described in U.S. Ser. No. 13/359,673, filed Jan. 27, 2012, and entitled "Restricted Wedge Suture Anchor and Method for Soft Tissue Repair".

FIGS. 10A and 10B show an isometric view and a cross sectional view of a suture anchor 700 respectively. The suture anchor 700 includes a suture locking portion 701 having a floating suture locking member 706.

The suture locking member 706, which has a cam shape, is held in the anchor by a pair of slots, nests or grooves 705 present in the anchor body. In particular, the cam 706 has a lateral portion that extends within groove 705, and the motion of cam 706 is restricted or directed by the shape of the groove 705. A second, mirror image nest (not shown) may be disposed on the opposite lateral side of anchor 700 so that a second portion or opposite lateral side or edge of the floating cam 706 may preferably be contained within this second nest.

As described in more detail below, the cam 706 is subjected to multiple degrees of freedom including a translational and rotational component as it moves from the open configuration to the locked configuration.

The floating cam 706 is shown in the open position in FIG. 10B, allowing a suture free end 28b to be pulled freely through the suture anchor 700. The cam 706 has a locking arm 708 and torque arm 709, disposed approximately on opposite sides of the intrinsic pivot point of the cam 706. The relative dimensions and angles of the locking arm and torque arm allow the torque arm to have a larger moment arm than the locking arm. (e.g., the torque arm 709 is longer than the locking arm 706). Therefore once tension from the bound end 28a reaches a sufficient level, calculate-able according to the relative moment arms between the two arms, the floating cam 706 may preferably move in a predominant clockwise direction to lock suture 28 within suture anchor 700; the locking surface 707 being an inferior side. Additional suture anchor designs having torque arms and cams are described in U.S. Ser. No. 13/359,631, filed Jan. 27, 2012, and entitled "Rotating Locking Member Suture Anchor and Method For Soft Tissue Repair".

Although the suture locking member 706 is shown having a cam shape, the invention is not so limited and the shape of the suture locking member may vary widely.

Additionally, although the slot shown in this embodiment has a bottom and does not extend completely through the anchor wall, the invention need not be so limited. The slot may extend completely through the anchor body wall and the invention is only intended to be limited as recited in the appended claims.

Methods for Tissue Repair

Figure 11:
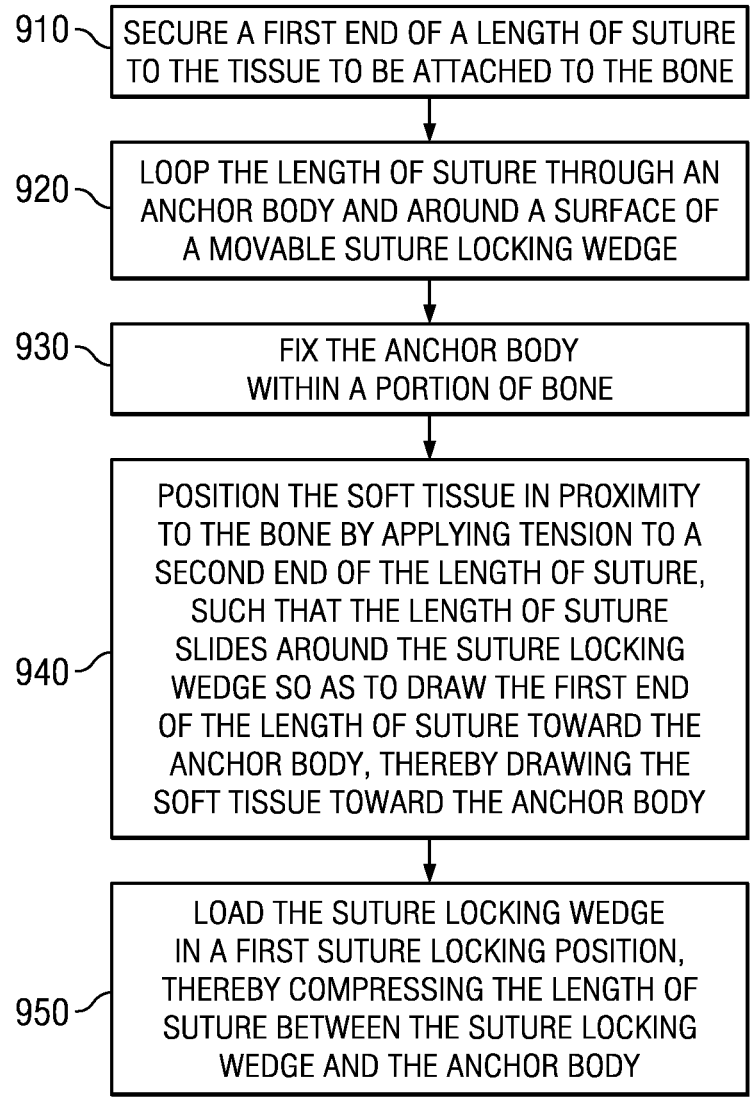
FIG. 11 illustrates a flow diagram of a method to secure connective tissue to bone.

FIG. 11 is a flowchart showing the steps of a medical procedure for securing connective tissue to bone. This procedure includes the steps of securing a first limb of a length of suture to a portion of connective tissue to be attached to a portion of bone, using any method deemed suitable to the clinician (Step 910).

Step 920 states to loop the length of suture through a lumen in a body of a suture anchor device and about a suture locking wedge disposed along the length of the lumen.

The suture anchor device may be temporarily attached to an insertion instrument shaft distal end, having an opening to provide a passage for the length of suture to gain access to the suture anchor device as described in previous figures. The shaft distal end may also have a driver to deploy an anchoring element, disposed at the proximal end of the anchoring device.

Next, the suture anchor is inserted into a portion of bone, deep enough so that the anchor device proximal end is in the cancellous bone region. A marker or indicator may be present on the shaft distal end to aid in proper anchor placement. The suture anchor is then deployed to fix the anchoring portion or anchoring element in surrounding bone (930).

Step 940 states to apply tension to the second limb of the length of suture, such that the length of suture slides around the suture locking wedge, so as to draw the first limb of the length of suture toward the suture anchor device, thereby drawing the connective tissue closer to the anchor thereby securing the portion of connective tissue snugly to the portion of bone.

Step 950 states to move the suture locking wedge to a first suture locking position, thereby compressing the suture at a first contact location between the suture locking wedge and the anchor body. The movement preferably comprises rotation and translation.

This step may be carried out by modifying the tension on the second limb (e.g., pausing, adjusting, or releasing tension on the free limb) so as to allow the tension on the tissue bound end to move the suture locking wedge.

Should the connective tissue need to be relocated, tension may be increased to the second length of suture (e.g., the free limb), sufficient enough to move the suture locking wedge so as to increase the gap and allow the length of suture to slide around the suture locking wedge, such that the soft tissue may be re-positioned relative to the portion of bone. After the connective tissue has been relocated, the tension may then be increased to the first limb of the length of suture again, so as to compress the suture again. The insertion instrument may then be removed from the area.

In another embodiment the step of applying tension on the second limb of the suture to unseat the suture locking wedge is performed subsequent to step 950 to release the suture from being compressed.

In another embodiment the method further comprises repeating steps 940 and 950 to reposition the soft tissue and to re-tension the suture. Applying tension may be performed by pulling on the second limb of the suture by hand or otherwise.

Figure 12:
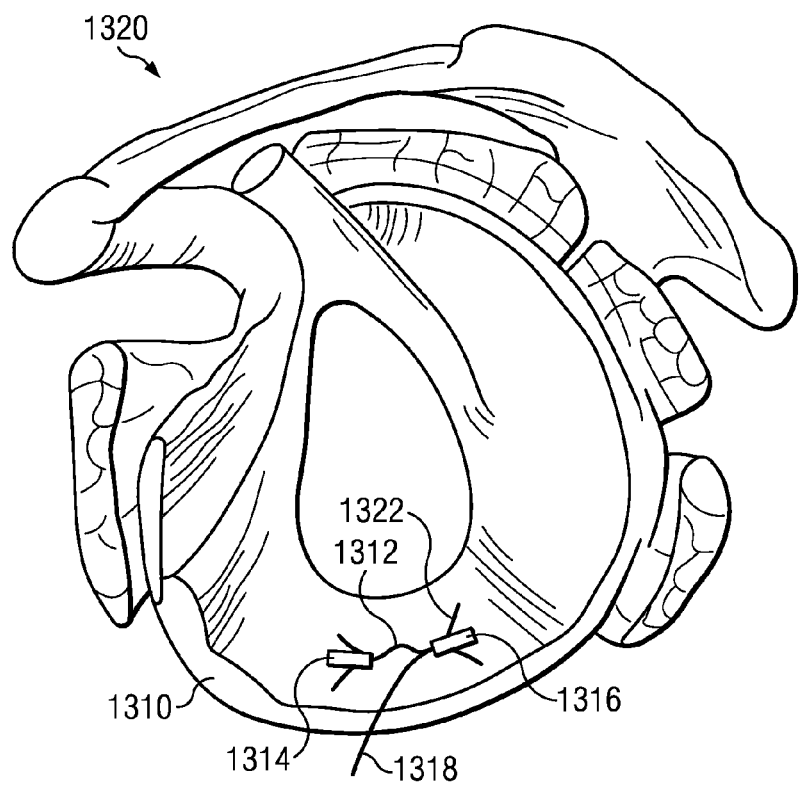
FIG. 12 is an illustration of a method for repairing a capsular tissue.

FIG. 12 illustrates a method for repairing capsular tissue. As shown, a glenoid section 1320 of a shoulder joint includes capsular tissue 1310. The capsular tissue 1310 serves to hold the humeral head in the shoulder joint. It should not be loose. However, if the capsular tissue is stretched (e.g., due to injury) the shoulder becomes loose. This is undesirable.

Repairing the capsule may be performed by stitching folds in the capsule to shrink its effective size (namely, plication). Tightening the capsule to the proper degree makes the shoulder more stable. Folds may be stitched in various manners. In one embodiment, and with reference to FIG. 12, a method comprises securing a first limb of a suture 1312 to a first anchor 1314.

A second limb of the suture 1312 is threaded or looped through a second anchor 1316. The anchors may have features similar to the anchors described herein. In the anchors shown in FIG. 12, radially deflectable members 1322 fix the anchor to the tissue.

Next, the first anchor 1314 and second anchor 1316 are placed in the tissue 1310 and connected with suture 1312. FIG. 12 shows the anchors separated by a region. Suture 1312 can be tightened incrementally by pulling on free suture limb or tail 1318. The amount of tension applied to the suture 1312 decreases the size of the region, tightening the capsule tissue 1310. This affects the stability and range of motion in the joint. The method thus allows the surgeon to increase tensions until a suitable stabilization is achieved that does not affect range of motion.

Figure 13:
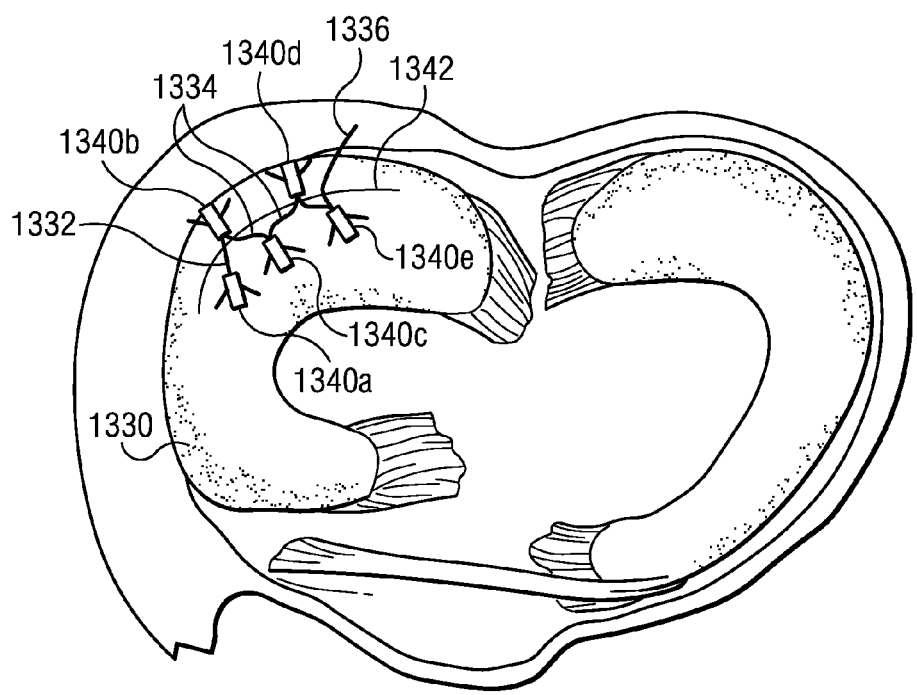
FIG. 13 is an illustration of a method for repairing a meniscus.

FIG. 13 illustrates another method for repairing soft tissue and in particular, a method for repairing a radial tear 1342 in the lateral meniscus 1330 of a knee.

Initially, the method comprises securing a first limb 1332 of a length of suture to a first anchor 1340a.

Next, the suture is looped or threaded through additional anchors 1340b, 1340c, 1340d, and 1340e such that a free suture limb 1336 extends from the last-threaded anchor. In the embodiment shown in FIG. 13, anchor 1340e is the last anchor of the sequence of anchors and free suture limb 1336 is shown extending therefrom. Although five anchors are shown in FIG. 13, the number may vary. In a preferred embodiment, the number of anchors placed ranges from 2-10. Generally, fewer anchors would preferably, but not necessarily, be deployed to close a smaller tear. More anchors (e.g., 6 or more) would preferably, but not necessarily, be deployed to close a larger tear.

Next, anchors 1340a, b, c, d, e are placed, one at a time, in the tissue such that the suture length extending between any two anchor bodies spans the tear. For example, anchor 1340b is next or adjacent in sequence to 1340a and the suture portion 1332 between the anchors 1340a and 1340b is shown spanning tear 1342.

Next, the physician pulls on the free suture limb 1336. This step places tension on the suture spanning the tear 1342, closing the tear so that it may heal.

Other modifications and variations can be made to the disclosed embodiments without departing from the subject invention. For example, other methods for anchor deployment will be apparent to the skilled artisan. Moreover, the instruments and methods described herein may be utilized in other regions of the body (e.g., knee, hip, etc.) and for other tissue treatment procedures. Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. An anchor device for repairing soft tissue with a suture, comprising:
    an anchor body comprising a wall, and the wall defining a lumen; and
    a suture locking wedge movably disposed within the lumen and engaged with the wall of the anchor body such that the suture locking wedge may move with a first degree of freedom and a second degree of freedom with respect to the lumen and such that when a first tension force is applied to a tissue limb of the suture extending through the anchor body and looped around the suture locking wedge, the suture locking wedge is urged into a suture locking position in which the suture is compressed between the suture locking wedge and a first contact location of the anchor body; and wherein the suture locking wedge has an elongate cross section that is moved from a more parallel orientation towards a more perpendicular orientation relative to an elongate axis of the anchor body when urged to the suture locking position.

2. The anchor device of claim 1 wherein the first degree of freedom is rotation.

3. The anchor device of claim 2 wherein the rotation is about an axis perpendicular to the longitudinal axis of the anchor device.

4. The anchor device of claim 3 wherein the second degree of freedom is translation in a direction parallel to the longitudinal axis.

5. The anchor device of claim 1 wherein said anchor body further comprises a bone fixation structure for securing the anchor device in the bone wherein the bone fixation structure is selected from the group consisting of threads, ridges, barbs, and wings.

6. The anchor device of claim 1 further comprising a gap between the suture locking wedge and the first contact location of the anchor body such that the suture locking wedge remains substantially free floating when not in the suture locking position.

7. The anchor device of claim 6 further comprising a flexible tether extending between the suture locking wedge and the anchor body.

8. The anchor device of claim 1 wherein the anchor body comprises an elastic section which deforms when the suture locking wedge is placed in the suture locking position.

9. The anchor device of claim 1 wherein the suture locking wedge and the lumen of the anchor body have complimentary engaging surfaces such that when the suture locking wedge is urged into the suture locking position, the suture locking wedge compresses the suture at a second contact location of the anchor body in addition to the first contact location.

10. The anchor device of claim 9 wherein the first contact location and the second contact location are on opposite walls of the lumen.

11. The anchor device of claim 1 wherein the suture locking wedge comprises a first arm and a second arm, the first arm having a different length than the second arm.

12. The anchor device of claim 1 wherein the suture locking wedge is movably disposed within the anchor body such that when a second tension force is applied to a free limb of the suture the suture locking wedge is urged away from the first contact location such that the suture is not compressed and can slide freely around the suture locking wedge.

13. An anchor device for repairing soft tissue with a suture, the anchor device comprising:
   an anchor body comprising an inner wall wherein the inner wall defines a lumen, and said inner wall further defines at least one window; and
   a suture locking wedge rotatably and translatably movable within the lumen and engaged with the at least one window of the anchor body such that the suture locking wedge is movable between a first position and a second position, and such that when a tension force is applied to a tissue limb of the suture extending through the anchor body and looped around the suture locking wedge, the suture locking wedge is urged into the first position in which the suture is compressed between the suture locking wedge and a first contact location of the anchor body; and wherein the suture locking wedge has an elongate cross section defining an approximately uniform width and an elongate cross section axis that is moved from a more parallel orientation towards a more perpendicular orientation relative to an elongate axis of the anchor body when urged to the first position.

14. The anchor device of claim 13 wherein the suture locking wedge comprises at least one extension member extending laterally from an edge of the suture locking wedge and sized to interface with the at least one window.

15. The anchor device of claim 13 wherein the suture locking wedge comprises two substantially planar surfaces which contact the suture.

16. The anchor device of claim 13 wherein the suture locking wedge has a height that is less than or equal to ½ the diameter of the suture.

17. The anchor device of claim 14 wherein said at least one extension member comprises a plurality of pins.

18. The anchor device of claim 13 wherein the at least one window comprises a plurality of regions.

19. The anchor device of claim 18 wherein the plurality of regions comprises a first region corresponding to the suture locking wedge in the first position and a second region overlapping with the first region and corresponding to the suture locking wedge in the second position.

20. The anchor device of claim 19 wherein the first region has a trapezoidal shape.

21. The anchor device of claim 20 wherein the first region comprises a first distal flat section which forms a first suture locking wedge angle with a radial axis of the anchor device, and said first suture locking wedge angle ranges from 15 to 30 degrees.

22. The anchor device of claim 21 wherein the second region comprises a second distal flat section which forms a second suture locking wedge angle with the radial axis of the anchor device, and said second suture locking wedge angle ranges from 5 to 15 degrees less than the first suture locking wedge angle.

23. The anchor device of claim 22 wherein second suture locking wedge angle is about 15 degrees.

24. The anchor device of claim 13 wherein the suture locking wedge comprises an elastic section which deforms when the suture locking wedge is placed in the first position.

25. The anchor device of claim 13 wherein the suture locking wedge and the anchor body have complimentary engaging surfaces such that when the suture locking wedge is urged into the first position, the suture locking wedge compresses the suture at a second contact location of the anchor body in addition to the first contact location.

26. The anchor device of claim 25 wherein the first contact location and the second contact location are on opposite walls of the lumen.

27. The anchor device of claim 13 wherein the anchor device comprises only two discrete parts not including the suture.

28. The anchor device of claim 13 wherein the at least one window is uncovered.

29. The anchor device of claim 13 further comprising a flexible tether extending between the suture locking wedge and the anchor body.

30. The anchor device of claim 13 wherein the anchor body and the suture locking wedge cooperate to translate in addition to rotate.

31. The anchor device of claim 13 wherein the suture locking wedge is movably disposed within the anchor body such that when a second tension force is applied to a free limb of the suture the suture locking wedge is urged away from the first contact location such that the suture is not compressed.

* * * * *